US012073570B2

(12) United States Patent
Shimizu

(10) Patent No.: US 12,073,570 B2
(45) Date of Patent: Aug. 27, 2024

(54) VIDEO GENERATION DEVICE

(71) Applicant: CITIZEN WATCH CO., LTD., Tokyo (JP)

(72) Inventor: Hideki Shimizu, Saitama (JP)

(73) Assignee: CITIZEN WATCH CO., LTD., Tokyo (JP)

( * ) Notice: Subject to any disclaimer, the term of this patent is extended or adjusted under 35 U.S.C. 154(b) by 371 days.

(21) Appl. No.: 17/638,697

(22) PCT Filed: Aug. 26, 2020

(86) PCT No.: PCT/JP2020/032226
§ 371 (c)(1),
(2) Date: Feb. 25, 2022

(87) PCT Pub. No.: WO2021/039857
PCT Pub. Date: Mar. 4, 2021

(65) Prior Publication Data
US 2022/0335625 A1 Oct. 20, 2022

(30) Foreign Application Priority Data

Aug. 29, 2019 (JP) ................. 2019-156804

(51) Int. Cl.
G06T 7/246 (2017.01)
G06T 7/215 (2017.01)
H04N 5/262 (2006.01)
(52) U.S. Cl.
CPC .............. *G06T 7/251* (2017.01); *G06T 7/215* (2017.01); *H04N 5/2621* (2013.01); *G06T 2207/10016* (2013.01)
(58) Field of Classification Search
None
See application file for complete search history.

(56) References Cited

U.S. PATENT DOCUMENTS 9,953,215 B2 *  4/2018  Auge ..................... G06V 20/64
10,277,834 B2 *  4/2019  Greenberger ........ H04N 5/2621
(Continued)

FOREIGN PATENT DOCUMENTS

JP  H11-133987 A   5/1999
JP  H11-212582 A   8/1999
(Continued)

OTHER PUBLICATIONS

Chan et al.("Everybody Dance Now", 1, 7-12 A arXiv, Aug. 27, 2019, 2-6 https://arxiv.org/pdf/1808.07371. df, retrieval date: Nov. 18, 2020) cited in IDS and provided by applicant (Year: 2020).*
(Continued)

*Primary Examiner* — Anand P Bhatnagar

(57) ABSTRACT

A subject who dances is motivated to participate in dancing by presenting an ideal dance video to the subject in the form of a virtual video of the subject. A video generation device (3) includes storage (70) that contains ideal skeletal pose information representing, for each of predetermined rhythms, a series of skeletal poses corresponding to ideal movements performed at predetermined timings to the predetermined rhythm; a recorder (20) that records an actual video of movements performed by a subject at predetermined timings to a predetermined rhythm played back; a skeletal-pose analysis unit (31) that extracts skeletal pose information representing a series of skeletal poses corresponding to the movements performed by the subject at predetermined timings from a group of still images constituting the actual video; a model generation unit (42) that generates a trained model of images of the subject corresponding to skeletal poses, based on the group of still images and the skeletal pose information; and a video generation unit (44) that generates and outputs a virtual ideal video, based on the trained model and the ideal skeletal pose information. The virtual ideal video is a video of the subject (Continued)

performing movements matching the ideal skeletal pose information at predetermined timings.

12 Claims, 16 Drawing Sheets

(56) References Cited

U.S. PATENT DOCUMENTS

| | | | | |
|---|---|---|---|---|
| 11,120,559 | B2* | 9/2021 | Goncharov | G06T 7/20 |
| 11,132,533 | B2* | 9/2021 | Dreessen | G06V 10/751 |
| 11,270,461 | B2* | 3/2022 | Tsang | G06T 7/74 |
| 11,295,119 | B2* | 4/2022 | Andreou | G06N 3/08 |
| 11,675,418 | B2* | 6/2023 | Fukumoto | A63F 13/428 |
| | | | | 345/418 |
| 2014/0285517 | A1* | 9/2014 | Park | G06T 13/40 |
| | | | | 345/632 |
| 2016/0042652 | A1 | 2/2016 | Nagai et al. | |
| 2018/0198990 | A1* | 7/2018 | Greenberger | H04N 5/2621 |
| 2018/0357472 | A1* | 12/2018 | Dreessen | G06V 20/49 |
| 2019/0269361 | A1 | 9/2019 | Shimizu | |
| 2020/0160046 | A1* | 5/2020 | Andreou | G06N 7/01 |
| 2020/0193671 | A1* | 6/2020 | Tamir | G06T 7/251 |
| 2022/0335625 | A1* | 10/2022 | Shimizu | A61B 5/16 |

FOREIGN PATENT DOCUMENTS

| | | |
|---|---|---|
| JP | 2000-209500 A | 7/2000 |
| JP | 2001-42880 A | 2/2001 |
| JP | 2002-269580 A | 9/2002 |
| JP | 2013-116311 A | 6/2013 |
| WO | 2014/162787 A1 | 10/2014 |
| WO | 2018/074371 A1 | 4/2018 |

OTHER PUBLICATIONS

WIPO, International Search Report for International Application No. PCT/JP2020/032226, Dec. 1, 2020.
WIPO, Written Opinion for International Application No. PCT/JP2020/032226, Dec. 1, 2020.
Zhe Cao, Tomas Simon, Shih-En Wei, Yaser Sheikh, "Realtime Multi-Person 2D Pose Estimation using Part Affinity Fields", [online], Nov. 24, 2016, [searched on Aug. 19, 2019] Internet <URL:https://arxiv.org/abs/1611.08050> (Described in the original specification of the present application as filed).
Chan, Caroline et al., "Everybody Dance Now", 1, 7-12 A arXiv, Aug. 27, 2019, 2-6 https://arxiv.org/pdf/1808.07371.pdf, retrieval date: Nov. 18, 2020, "abstract", "1 . Introduction" to "3. Method", fig. 3 (Cited in International Search Report and Written Opinion for International Application No. PCT/JP2020/032226 (Cite Nos. 1 and 2 of Non-Patent Literature Documents in this list) and described in the original specification of the present application as filed).
Fujimoto, Minoru et al., "A Dance Training System 1, 7-12 A that Maps Self-Images onto an Instruction Video", 2-6 ACHI 2012, The Fifth International Conference on Advances in Computer-Human Interactions, Feb. 4, 2012, pp. 309-314, https://www.thinkmind.org/index.php?view=article&articleid=achi-2012-12 30_20280, retrieval date:(Cited in International Search Report and Written Opinion for International Application No. PCT/JP2020/032226 (Cite Nos. 1 and 2 of Non-Patent Literature Documents in this list).

\* cited by examiner

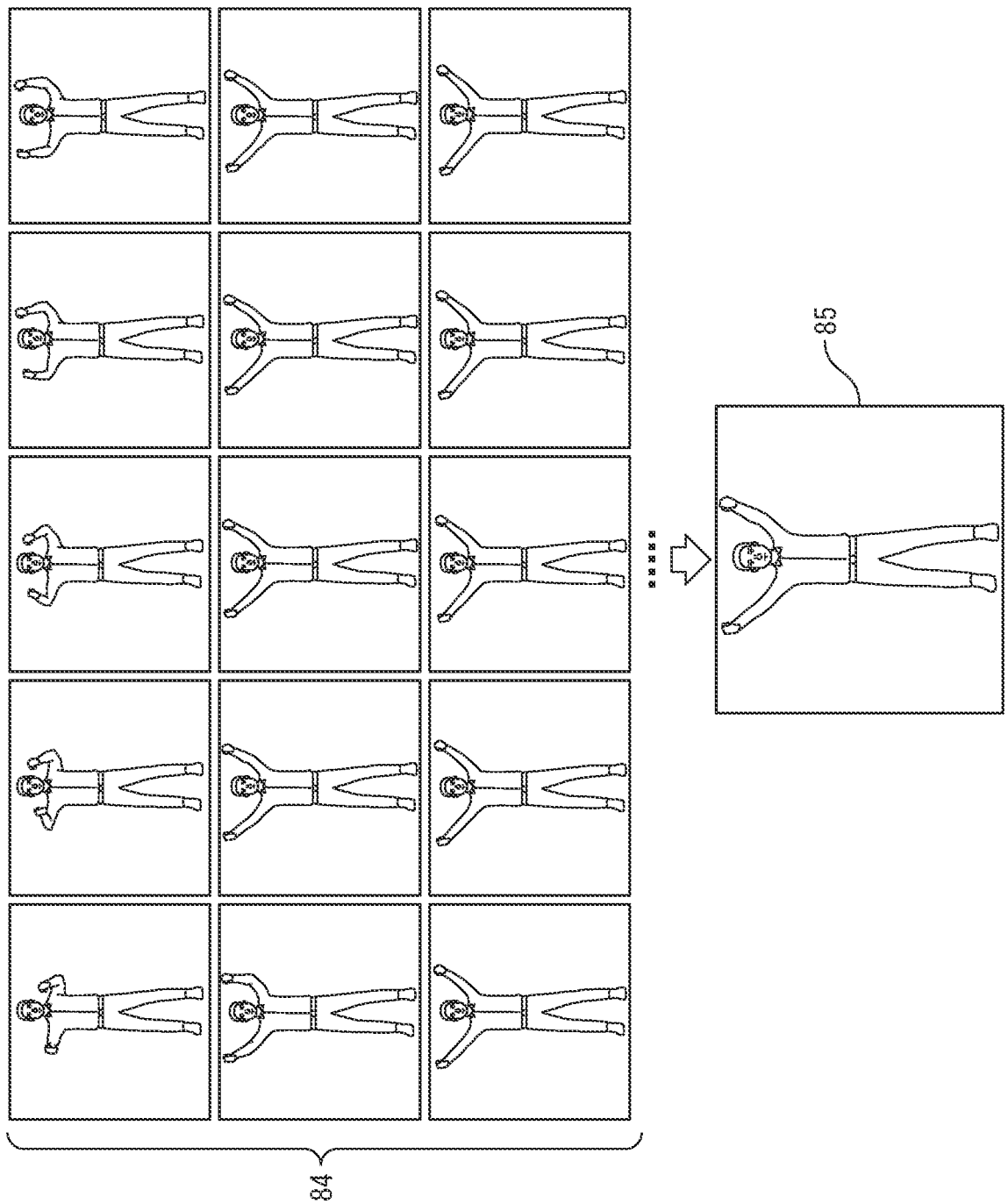

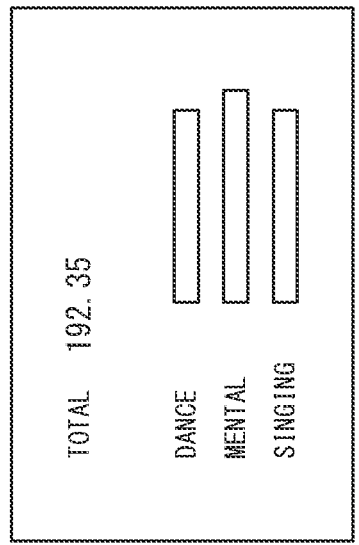
FIG. 10A
FIG. 10B
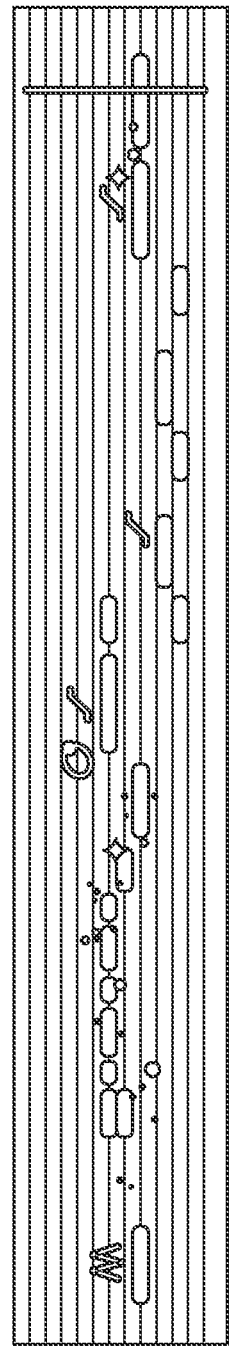
FIG. 10C

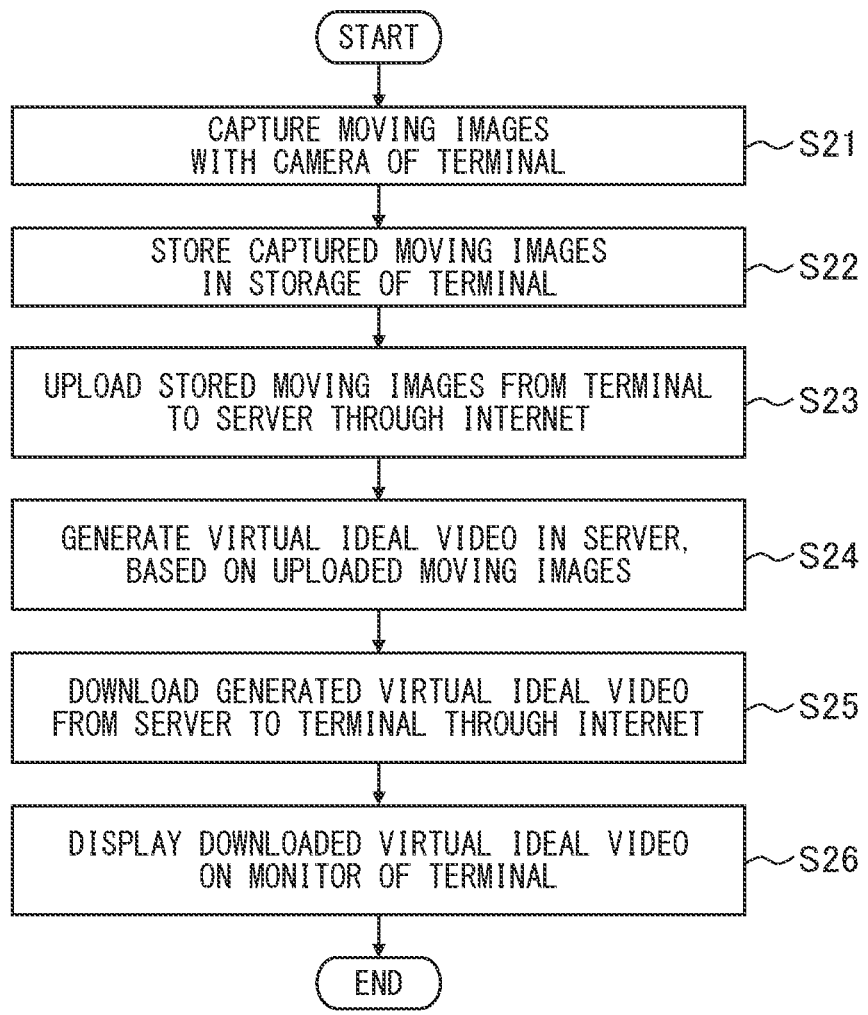

VIDEO GENERATION DEVICE

FIELD

The present invention relates to a video generation device.

BACKGROUND

A known karaoke device obtains positional information of a singer during karaoke, and compares it with reference choreographic data to grade movements and steps of the singer (see, e.g., Patent Literature 1 and 2). Another known karaoke device displays animation images of choreography of a piece of karaoke music, or combines a person's image with a video played back during singing and displays it (see, e.g., Patent Literature 3 to 5).

Patent Literature 6 describes a system for generating an animation. This system obtains motion parameters of parts constituting a three-dimensional model of a human body from a person in an obtained two-dimensional animation, generates a three-dimensional model, extracts texture data corresponding to each part, sets a viewpoint, and generates a two-dimensional animation from the three-dimensional model by interpolation using the texture data.

Non-patent Literature 1 describes a technique to detect the two-dimensional pose of people in an image by estimating the positions of joints with artificial intelligence (AI). Non-patent Literature 2 describes a technique to generate a video of a dancing person from a video of another person performing the same dance.

CITATION LIST

Patent Literature

Patent Literature 1: Japanese Unexamined Patent Publication No. 11-212582
Patent Literature 2: International Publication No. 2014/162787
Patent Literature 3: Japanese Unexamined Patent Publication No. 11-133987
Patent Literature 4: Japanese Unexamined Patent Publication No. 2000-209500
Patent Literature 5: Japanese Unexamined Patent Publication No. 2001-42880
Patent Literature 6: Japanese Unexamined Patent Publication No. 2002-269580

Non-Patent Literature

Non-patent Literature 1: Zhe Cao, Tomas Simon, Shih-En Wei, Yaser Sheikh, "Realtime Multi-Person 2D Pose Estimation using Part Affinity Fields", [online], Nov. 24, 2016, [searched on Aug. 19, 2019], Internet <URL: https://arxiv.org/abs/1611.08050>
Non-patent Literature 2: Caroline Chan, Shiry Ginosar, Tinghui Zhou, Alexei A. Efros, "Everybody Dance Now", [online], Aug. 22, 2018, [searched on Aug. 19, 2019], Internet <URL: https://arxiv.org/abs/1808.07371>

SUMMARY

With aging, services for maintaining health with enjoyment, such as dance karaoke and locomotive exercise, are growing. However, elderly people have low athletic ability, and in many cases, they do not keep going to dance karaoke for a long time and quit after participating only a couple of times because they cannot dance well and look inelegant. A device that grades dancing, such as a karaoke device that grades movements and steps, is known; but mere grading does not motivate participants and make them keep doing. To maintain health, ingenious design to motivate participants in dance karaoke is necessary.

It is an object of the present invention to motivate a subject who dances to participate in dancing by presenting an ideal dance video to the subject in the form of a virtual video of the subject.

Provided is a video generation device including storage (memory) that contains ideal skeletal pose information representing, for each of predetermined rhythms, a series of skeletal poses corresponding to ideal movements performed at predetermined timings to the predetermined rhythm; and a recorder that records an actual video of movements performed by a subject at predetermined timings to a predetermined rhythm played back. The video generation device further includes a skeletal-pose analysis unit (a skeletal-pose analyzer) that extracts skeletal pose information representing a series of skeletal poses corresponding to the movements performed by the subject at predetermined timings from a group of still images constituting the actual video; a model generation unit (a model generator) that generates a trained model of images of the subject corresponding to skeletal poses, based on the group of still images and the skeletal pose information; and a video generation unit (a video generator) that generates and outputs a virtual ideal video, based on the trained model and the ideal skeletal pose information. The virtual ideal video is a video of the subject performing movements matching the ideal skeletal pose information at predetermined timings.

The video generation device may further include a difference determination unit (a difference determiner) that determines difference between joint angles of skeletal poses of the skeletal pose information and the ideal skeletal pose information; and the video generation unit may output the virtual ideal video when the difference is not less than a reference value.

The video generation unit may select a section of the predetermined rhythm corresponding to the movements performed by the subject at predetermined timings, based on the magnitude of the difference, and play back the actual video and the virtual ideal video of the section in synchronization.

The difference determination unit may determine the difference for each of joints; and the video generation unit may select one of the joints, based on the magnitude of the difference, and play back the actual video and the virtual ideal video in synchronization, with a portion around the selected joint being enlarged.

The video generation device may further include a score calculation unit (a score calculator) that calculates a score of the movements performed by the subject at predetermined timings, depending on the magnitude of the difference.

The video generation device may further include a pulse-wave analysis unit (a pulse-wave analyzer) that extracts a pulse wave signal of the subject from time-series data indicating skin color of the subject in the actual video to calculate an index indicating the degree of variations in pulse intervals; and a feeling determination unit (a feeling determiner) that determines whether the subject has a negative feeling with brain fatigue, anxiety, or depression, or a positive feeling free from brain fatigue, anxiety, and depression, based on the index, and that calculates a score regarding feelings of the subject, depending on frequency of occurrence of the positive feeling during movements performed at predetermined timings.

The video generation device may further include a structure modification unit (a structure modifier) that calculates the ratio between the lengths of the trunk and the legs of the subject in the actual video and that modifies the lengths of the trunk and the legs of the skeletal poses in the ideal skeletal pose information, depending on the ratio; and the video generation unit may generate the virtual ideal video, based on the trained model and the modified ideal skeletal pose information.

The video generation device may further include an image extraction unit (an image extractor) that extracts some still images from the group of still images, based on a predetermined criterion regarding the angles or positions of joints of skeletal poses corresponding to the respective still images; and the model generation unit may generate the trained model, based on the extracted still images and skeletal poses in the skeletal pose information corresponding to the extracted still images.

The video generation device may further include an image processor that generates a virtual ideal video for the video generation unit.

The video generation device may further include a communication interface that receives an actual video of the subject from an external terminal and that transmits a virtual ideal video of the subject to an external terminal.

In the video generation device, the predetermined rhythms may be made by pieces of music.

In the video generation device, the movements performed at predetermined timings may be dance movements.

The video generation device can motivate a subject who dances to participate in dancing by presenting an ideal dance video to the subject in the form of a virtual video of the subject.

BRIEF DESCRIPTION OF DRAWINGS

FIG. 8 is a diagram for explaining the functions of a video generation unit 44.

FIGS. 10A to 10C illustrates examples of display of a dance score and a mental score.

FIG. 16 is a flowchart for explaining the steps of operation of the video generation device according to the fourth embodiment of the present disclosure.

DESCRIPTION OF EMBODIMENTS

A video generation device according to an embodiment of the present disclosure will now be described with reference to the attached drawings. However, note that the present invention is not limited to the drawings or the embodiments described below. The following describes an example in which a predetermined rhythm is made by a piece of music and movements performed at predetermined timings to the predetermined rhythm are dance movements.

The video generation device generates an ideal dance video, which is a video of a dancing subject whose movements and poses are the same as those of a dancing master (instructor), and presents it to the subject. This virtually generated ideal dance video will hereafter be referred to as a "virtual ideal video". In particular, the video generation device calculates a score of dance movements from skeletal poses of the subject performing dance movements, and, when the score is low, determines that he/she cannot dance well, and presents the virtual ideal video. The device shows poses as they should be in the form of the subject's video rather than the master's video, thereby enhancing the subject's motivation to keep dancing. Additionally, the video generation device determines the category of the subject's feeling (whether he/she feels brain fatigue or anxious or depressed) from face images of the subject performing dance movements, and also evaluates the subject's feeling, enabling the subject to find a piece of music to which he/she can dance well with fun.

The following description will be given by taking a dance performed in the scene of karaoke as an example; but the video generation device is usable in the scene of practice of any dance, and the type of dance is not specifically limited.

First Embodiment

Figure 1:
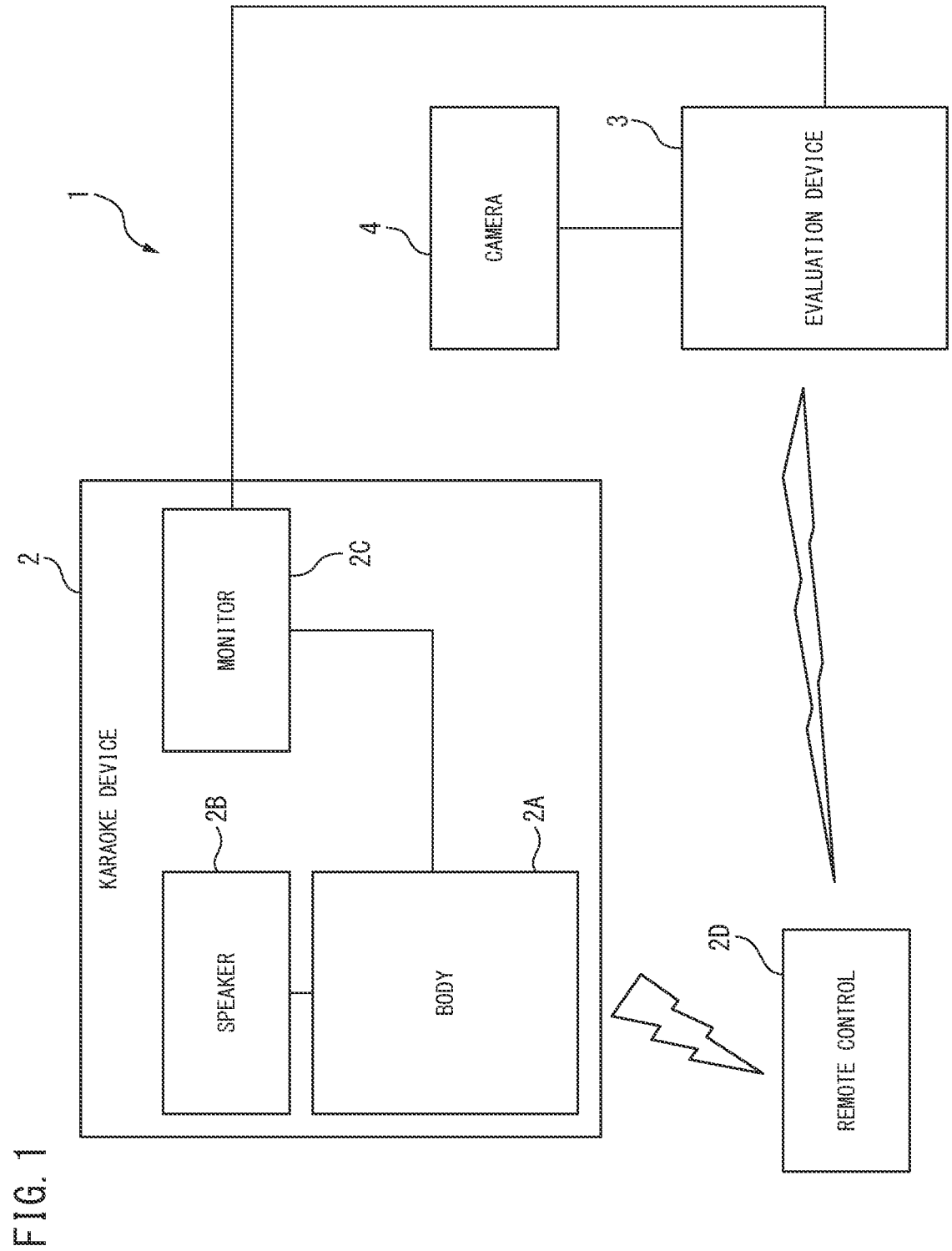
FIG. 1 illustrates the general configuration of a karaoke system 1.
Figure 2:
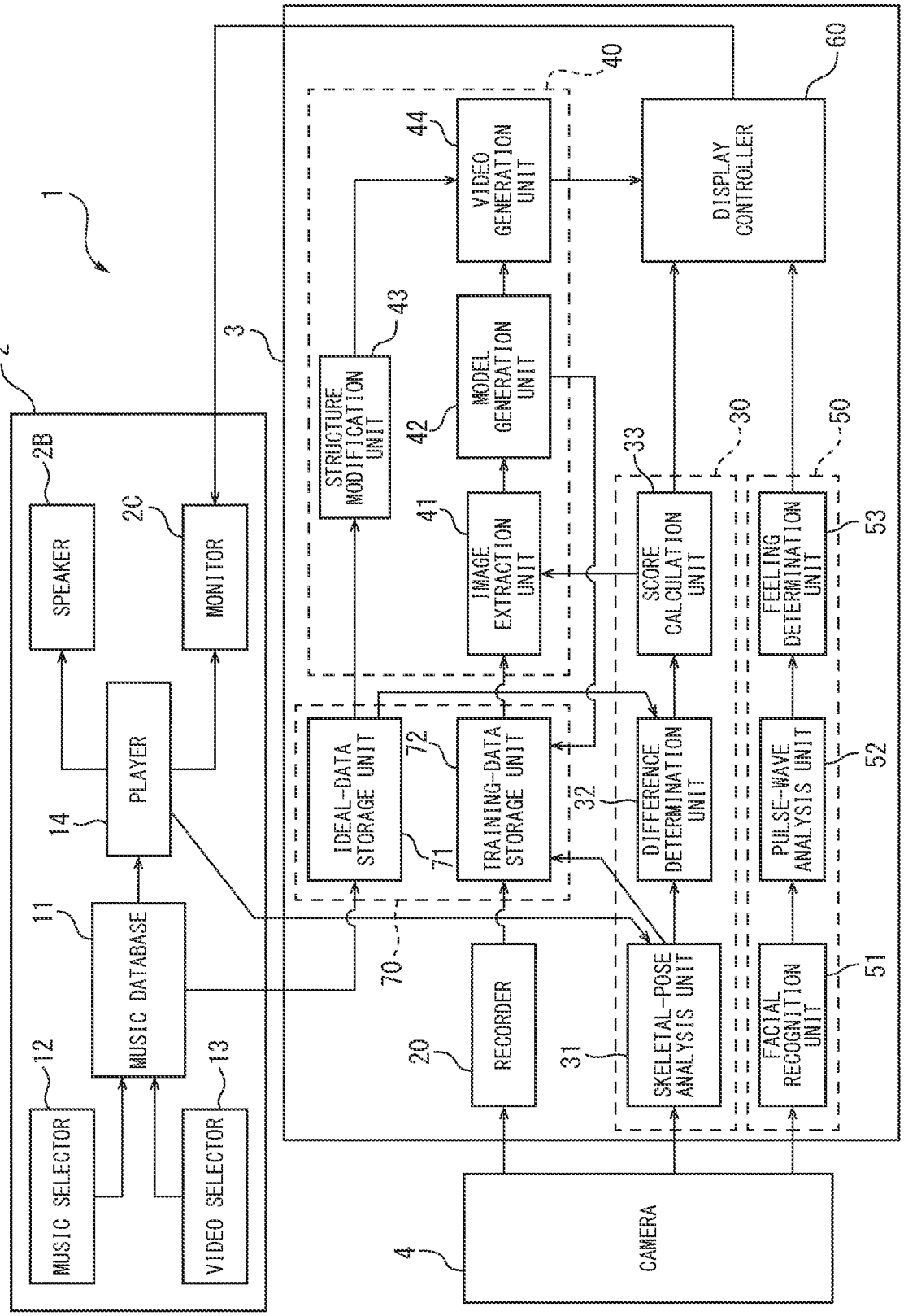
FIG. 2 is a functional block diagram of the karaoke system 1.

FIG. 1 illustrates the general configuration of a karaoke system 1 including a video generation device according to the first embodiment. FIG. 2 is a functional block diagram of the karaoke system 1. The karaoke system 1 is composed of a karaoke device 2, an evaluation device 3, and a camera 4. The karaoke device 2 is composed of a body 2A, a speaker 2B, a monitor 2C, and a remote control 2D. The karaoke device may further include a projector (not shown) and output a video to the projector rather than to the monitor 2C.

As its functional blocks, the body 2A includes a music database 11, a music selector 12, a video selector 13, and a player 14. The music database 11 is storage (memory) that contains pieces of karaoke music and videos. The music selector 12 and the video selector 13 select music and a video stored in the music database 11 in response to a user operating the remote control 2D. The player 14 outputs the music selected by the music selector 12 to the speaker 2B and the video selected by the video selector 13 to the monitor 2C, and plays them back.

The remote control 2D is a terminal for a user to select a piece of music, and is also used for operating the evaluation device 3. The evaluation device 3 is an example of the video generation device, and the camera 4 captures a video of a singer of a piece of music and a subject performing dance movements to a piece of music. FIG. 1 illustrates a configuration in which the evaluation device 3 and the camera 4 are added to the karaoke device 2 as an optional subsystem. In this case, the karaoke device 2 may be one commonly used today. However, all of the functions of the evaluation device 3 described below may be implemented in the karaoke device 2 as software, and the camera 4 may be one that the karaoke device includes from the beginning.

As its functional blocks, the evaluation device 3 includes a recorder 20, an analyzer 30, a generator 40, a feeling evaluator 50, a display controller 60, and storage 70. Of these, the storage 70 is constructed from, for example, a semiconductor memory or a hard disk whereas the other functional blocks are implemented by a computer program executed on a microcomputer including a CPU, a ROM, and a RAM.

The recorder 20 stores data of an actual video captured by the camera 4 in the storage 70 to record a video. The camera 4 and the recorder 20 record an actual video of dance movements performed by a subject (participant in dance karaoke) to a piece of music played back by the karaoke device 2.

The analyzer 30 is composed of a skeletal-pose analysis unit (a skeletal-pose analyzer) 31, a difference determination unit (a difference determiner) 32, and a score calculation unit (a score calculator) 33. The analyzer 30 analyzes skeletal poses of the subject in an actual video captured by the camera 4, determines the differences between individual joint angles of these skeletal poses and corresponding ideal values, and calculates a score of the dance movements (hereafter, a "dance score").

The skeletal-pose analysis unit 31 applies, for example, the technique described in Non-patent Literature 1 to each still image constituting the actual video captured by the camera 4 (for example, in the case of a 30-FPS video, thirty still images per second) to recognize the subject's skeletal pose. The skeletal pose is a two-dimensional skeleton composed of line segments representing the head, trunk, right arm, left arm, right leg, and left leg. Skeletal pose information is information on relative positions and relative angles of these segments. Since the skeletal pose changes during dance movements, the skeletal pose information is defined in association with the elapsed time of playback of a piece of music. The skeletal-pose analysis unit 31 extracts skeletal pose information representing a series of skeletal poses corresponding to the subject's dance movements from a group of still images constituting the actual video, and stores a still image including an image of the actual video and a skeletal pose in juxtaposition in the storage 70 for each frame.

Figure 3:
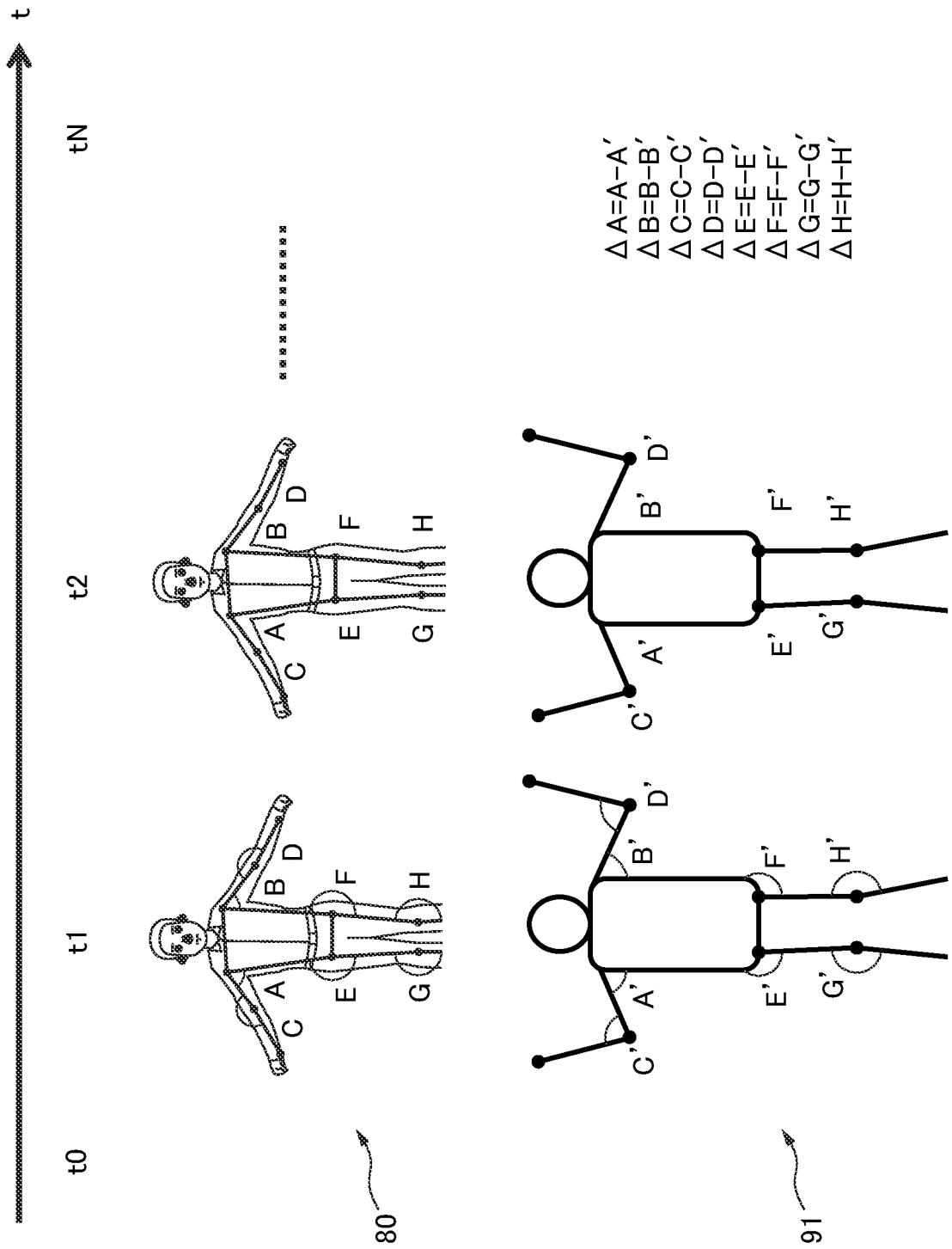
FIG. 3 is a diagram for explaining the functions of an analyzer 30.

FIG. 3 is a diagram for explaining the functions of the analyzer 30. Reference symbol t indicates the elapsed time; reference symbols t0 and tN indicate the start and end times of a piece of music, respectively; reference symbols t1 and t2 indicate different times during playback of the piece of music. Reference symbol 80 indicates an actual video of a subject, and thick lines superposed in the figure represent a skeletal pose recognized by the skeletal-pose analysis unit 31. Reference symbols A to H indicate joint angles of the right shoulder, left shoulder, right elbow, left elbow, right thigh, left thigh, right knee, and left knee in the subject's skeletal pose. In FIG. 3, reference symbol 91 indicates a skeletal pose of a master, and reference symbols A' to H' indicate joint angles in the master's skeletal pose.

The difference determination unit 32 determines the difference between joint angles of skeletal poses of skeletal pose information and ideal skeletal pose information. The ideal skeletal pose information, which is information representing a series of skeletal poses corresponding to ideal dance movements performed by a master to the same piece of music as the subject dances to, is linked to the music database 11, defined in association with the elapsed time in the piece of music, and prestored in the storage 70 for each piece of music. During playback of a piece of music, the difference determination unit 32 determines the difference between the subject's and the master's skeletal poses at the same time, for example, for each of the eight joint angles indicated by reference symbols A to H in FIG. 3, at certain intervals, e.g., every second. Each joint angle is an angle formed between line segments made by skeleton recognition. For example, the difference between angles of the right shoulder A is determined by $\Delta A = A - A'$. Capturing videos of the subject and the master at the same position and angle enables skeletal poses to be compared in this way, using the differences between angles in a two-dimensional image.

The score calculation unit 33 calculates a dance score of the subject, depending on the magnitude of the differences determined by the difference determination unit 32, and displays its value on the monitor 2C of the karaoke device 2. For example, the score calculation unit 33 calculates the dance score by expression "$100 - k(\Delta A_{ave} + \Delta B_{ave} + \Delta C_{ave} + \Delta D_{ave} + \Delta E_{ave} + \Delta F_{ave} + \Delta G_{ave} + \Delta G_{ave})$". $\Delta A_{ave}$ to $\Delta H_{ave}$ are averages of differences $\Delta A$ to $\Delta H$ obtained from the start time t0 until the end time tN of a piece of music regarding joint angles of the right shoulder, left shoulder, right elbow, left elbow, right thigh, left thigh, right knee, and left knee indicated by reference symbols A to H in FIG. 3, respectively, and k is an appropriate factor. However, this expression is merely an example, and the dance score is appropriately defined so as to increase as the differences between joint angles decrease.

Figure 4:
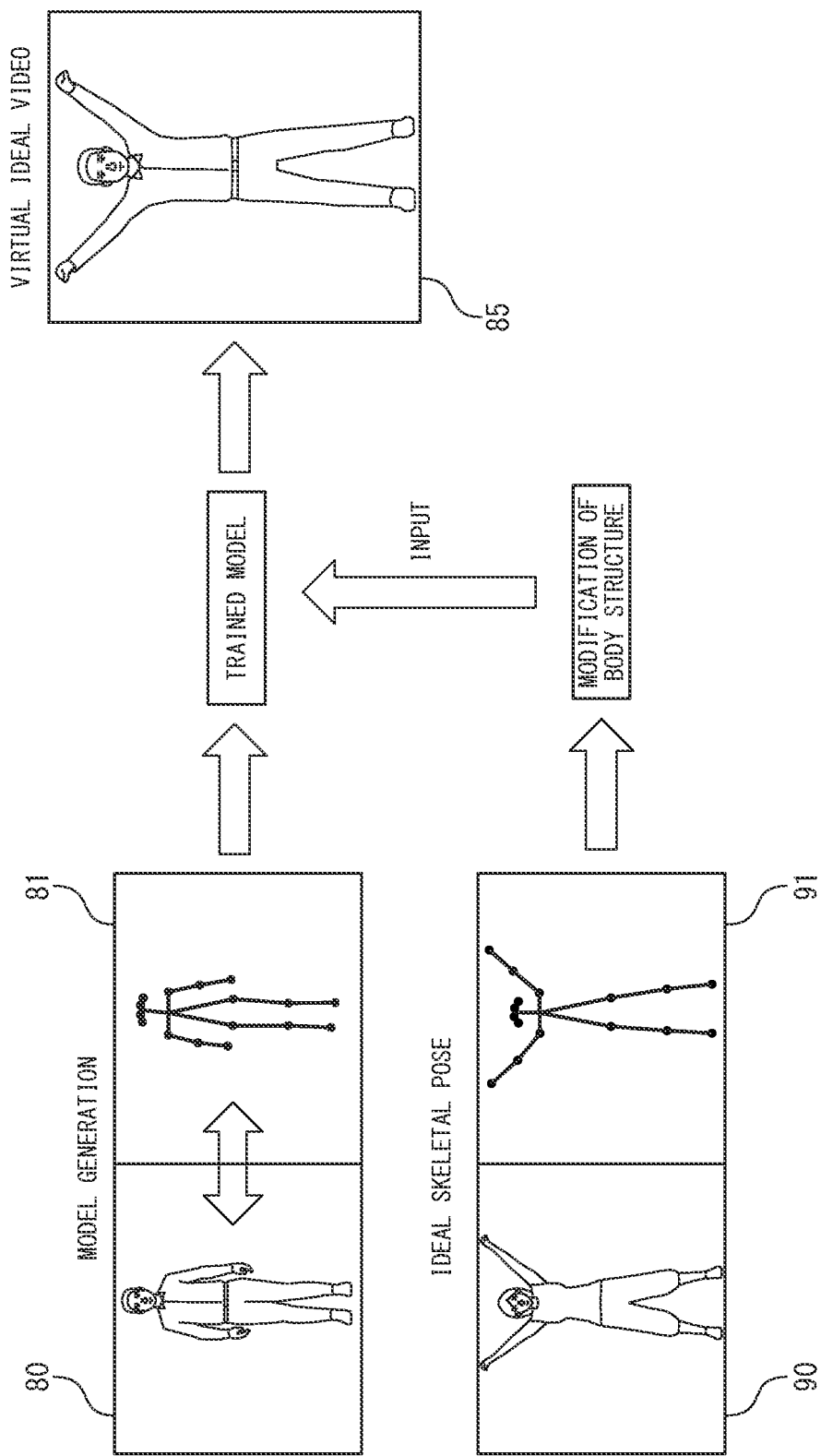
FIG. 4 is a diagram for explaining the functions of a generator 40.

FIG. 4 is a diagram for explaining the functions of the generator 40. In FIG. 4, reference symbols 80 and 81 indicate an actual video and a skeletal pose of the subject whereas reference symbols 90 and 91 indicate an actual video and a skeletal pose of the master. When the dance score calculated by the score calculation unit 33 is not higher than a reference value, the generator 40 learns the relationship between the actual video 80 and the skeletal pose 81 of the subject to generate a trained model. The generator 40 then modifies the prestored ideal skeletal pose information to match it to the subject's body structure, and generates a virtual ideal video 85, which is a video of the subject performing the same dance movements as the master, based on the trained model and the modified ideal skeletal pose information.

The generator 40 is composed of an image extraction unit (an image extractor) 41, a model generation unit (a model generator) 42, a structure modification unit (a structure modifier) 43, and a video generation unit (a video generator) 44, as shown in FIG. 2. The image extraction unit 41 extracts (selects) some still images to be used by the model generation unit 42 for generating a trained model, from the group of still images stored in the storage 70. In view of use in the scene of karaoke, it is desirable to finish video generation at most approximately 30 minutes. However, since the number of still images constituting a several-minute video is several thousand or more, learning with all of them takes an extremely long time. Additionally, since many of still images constituting a video are similar images, not all of them are necessary for learning, and several tens of images are enough. Thus, to speed up learning, the image extraction unit 41 selects several tens of still images representing greatly different skeletal poses.

Figure 5:
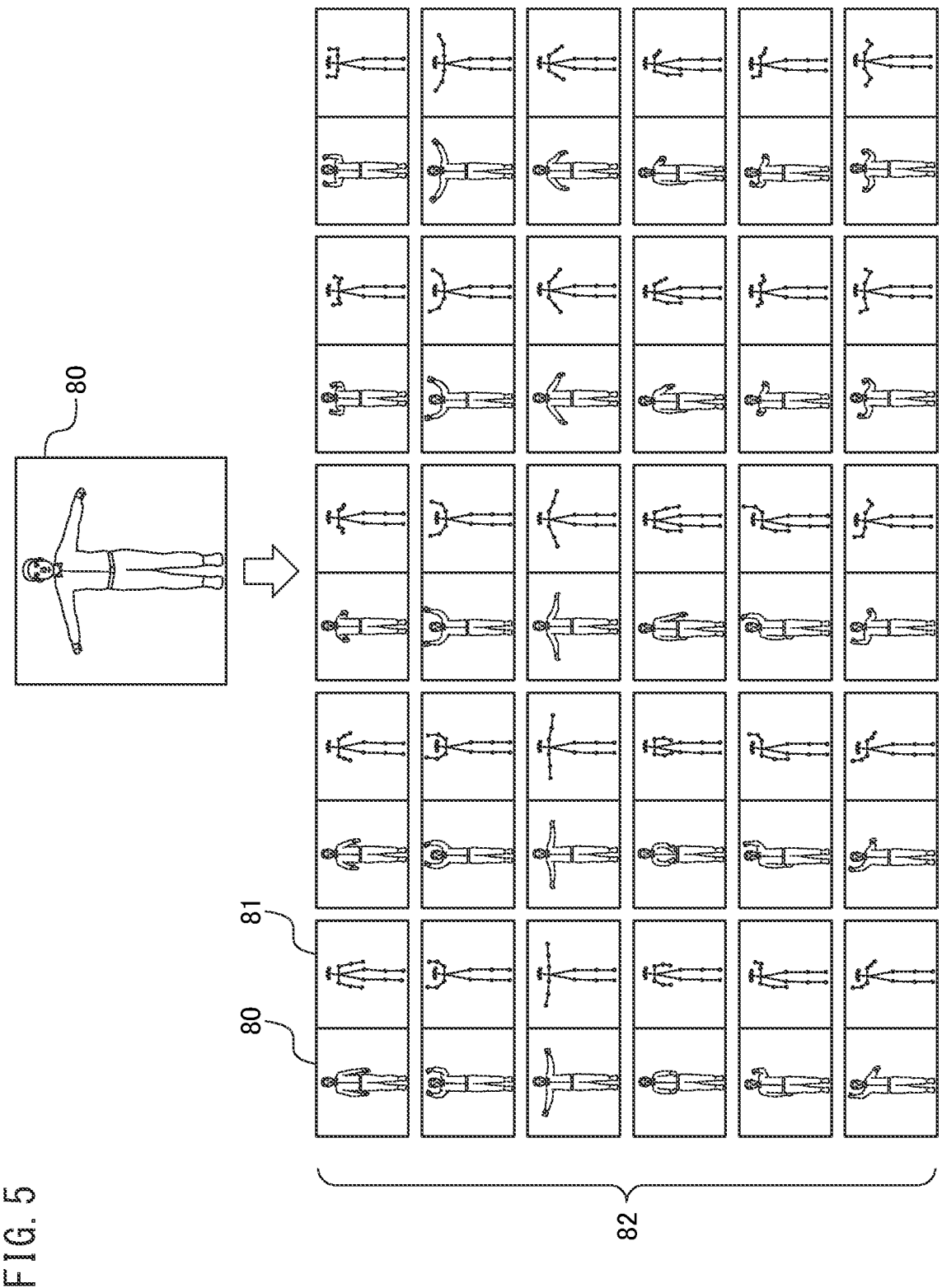
FIG. 5 is a diagram for explaining the functions of an image extraction unit 41.
Figure 6:
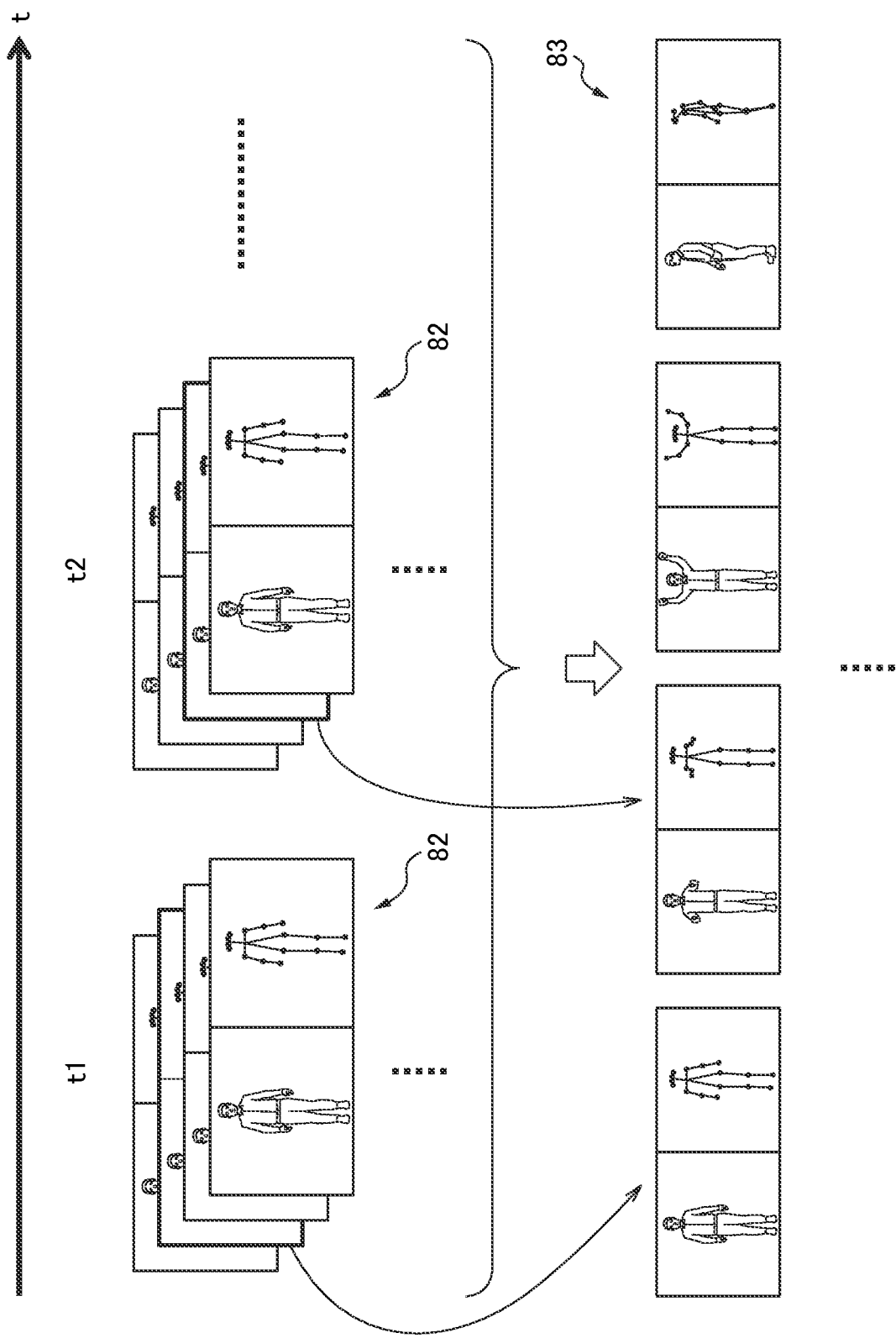
FIG. 6 is a diagram for explaining the functions of the image extraction unit 41.

FIGS. 5 and 6 are diagrams for explaining the functions of the image extraction unit 41. FIG. 5 shows a group of still images 82 constituting the subject's actual video 80. For example, a 30-FPS video includes thirty still images per second. The skeletal-pose analysis unit 31 recognizes a skeletal pose 81 every frame of the video, and generates a group of image data including still images and skeletal poses in juxtaposition. Further, as shown in FIG. 6, the image extraction unit 41 extracts some still images 83 from the group of still images 82, based on a predetermined criterion regarding the angles or positions of joints of skeletal poses corresponding to the respective still images.

For example, the image extraction unit 41 first selects an image, and then selects another image such that the coordinates of the right arm or the joint angle of the right shoulder or elbow differs from that in the first image by more than a reference value. Additionally, regarding the left arm, right leg, and left leg, the image extraction unit 41 similarly selects images such that coordinates or a joint angle differs by more than the reference value, up to several tens of images in total. Alternatively, the image extraction unit 41 may determine averages of the coordinates and the joint angles of, for example, the right arm, left arm, right leg, and left leg every second, and select several tens of images such that the coordinates and the joint angles of the right arm, left arm, right leg, and left leg differ from these averages by more than reference values. Alternatively, the image extraction unit 41 may select still images at random from the group of still images regardless of the angles and positions of joints. The number of still images extracted by the image extraction unit 41 is, for example, 20, 25, or 30, and is selected appropriately, depending on the throughput of the hardware of the evaluation device 3, so that the model generation unit 42 will finish learning within several tens of minutes.

The model generation unit 42 executes deep learning of the relationship between skeletal poses and images of the subject, based on the still images extracted by the image extraction unit 41 and the skeletal poses corresponding thereto, thereby generating a trained model of images of the subject corresponding to skeletal poses. To achieve this, the model generation unit 42 following, for example, the technique described in Non-patent Literature 2 uses Pix2Pix, which is an open-source algorithm. Pix2Pix, which is a type of image generation algorithm using generative adversarial networks, learns the relationship between a pair of images and generates a counterpart from an image by interpolation taking account of this relationship. The model generation unit 42 stores the trained model in the storage 70.

The structure modification unit 43 calculates the ratio between the lengths of the trunk and the legs (thighs and shanks) of the subject in the actual video 80, and modifies the lengths of the trunk and the legs of the skeletal poses in the ideal skeletal pose information, which is used by the video generation unit 44 to generate the virtual ideal video 85, depending on the ratio. For example, if the length of the subject's legs relative to his/her trunk is greater than the relative length of the master's legs, the structure modification unit 43 extends only the legs of the skeletal poses in the ideal skeletal pose information by the ratio of the subject's legs with the arms and trunk kept unchanged. A large difference in height between the subject and the master may cause an image generated by the video generation unit 44 to look unnatural as if it were extended or compressed; the body structure is modified to prevent this.

The video generation unit 44 generates a virtual ideal video of the subject, based on the trained model generated by the model generation unit 42 and the ideal skeletal pose information stored in the storage 70 in association with the same piece of music as the subject dances to (and modified by the structure modification unit 43). To achieve this, the video generation unit 44 following, for example, the technique described in Non-patent Literature 2 uses Pix2Pix, similarly to the model generation unit 42. The virtual ideal video generated by the video generation unit 44 is a video of a person who performs dance movements matching the ideal skeletal pose information (i.e., the arms and the legs move like those of the master) and whose face, body structure, and clothing are the same as those of the subject (a video in which everything except for movements is changed from the master's to the subject's).

Figure 7:
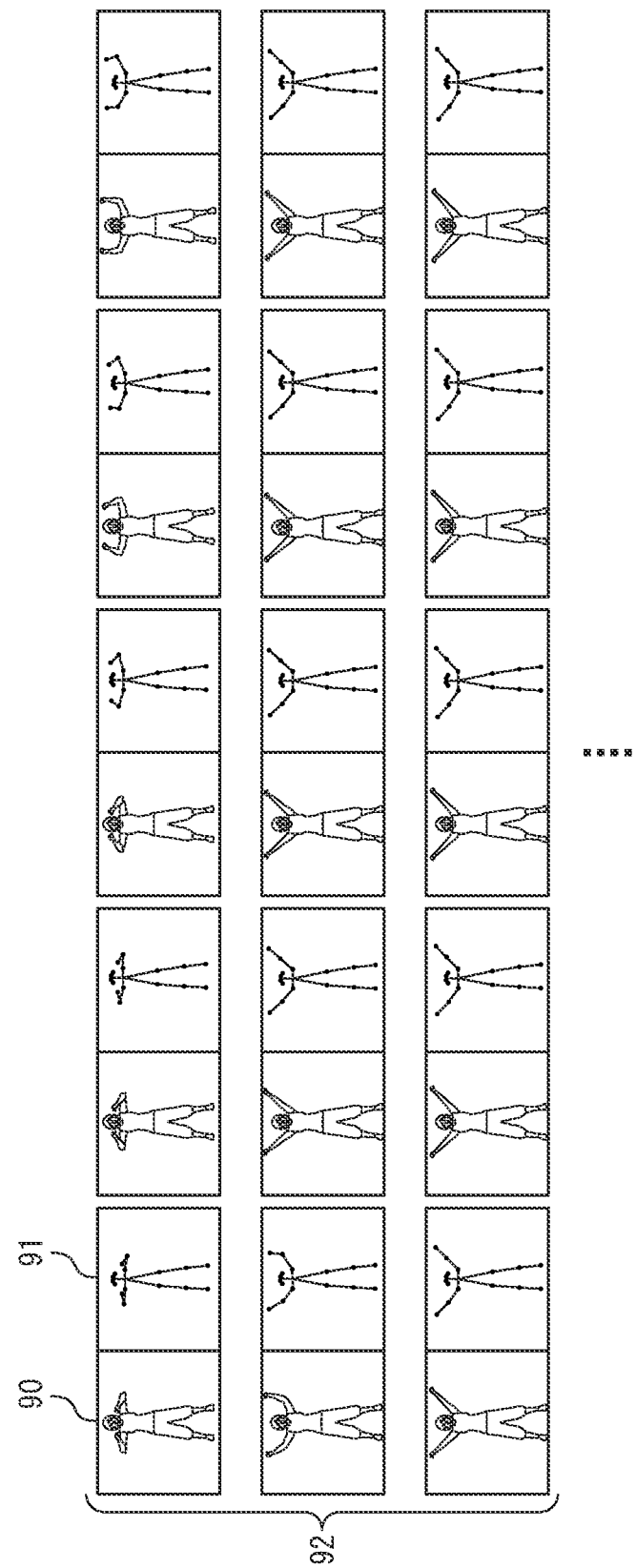
FIG. 7 illustrates an example of ideal skeletal pose information.

FIG. 7 illustrates an example of the ideal skeletal pose information. FIG. 8 is a diagram for explaining the functions of the video generation unit 44. As shown in FIG. 7, the ideal skeletal pose information is a group of still images (group of image data) 92 including the still images in the actual video 90 and the skeletal poses 91 of the master's ideal dance movements in juxtaposition. The group of still images 92 includes all of the still images corresponding to dance movements from the beginning to the end of a piece of music. The video generation unit 44 inputs the ideal skeletal pose information regarding a target piece of music into the trained model to generate a virtual group of still images 84, as shown in FIG. 8, representing skeletal poses identical to the master's, and converts it into moving images to generate the virtual ideal video 85.

The video generation unit 44 outputs the virtual ideal video, for example, when the dance score calculated by the score calculation unit 33 is lower than a reference value, i.e., when the subject cannot dance well and the difference between joint angles calculated by the difference determination unit 32 is not less than a reference value. The video generation unit 44 plays back only the virtual ideal video, or the actual video captured by the camera 4 and the virtual ideal video in juxtaposition, on the monitor 2C of the karaoke device 2. However, the video generation unit 44 may display the virtual ideal video on the monitor 2C regardless of the dance score. In this case, calculation of the dance score by the score calculation unit 33 may be omitted.

The video generation unit 44 may play back the virtual ideal video only in a portion of the target piece of music where the difference between skeletal poses of the subject and the master is large, rather than in the whole piece of music. In this case, for example, the video generation unit 44 may select a section of the piece of music where the dance score calculated by the score calculation unit 33 is lower than the reference value, and play back the actual video and the virtual ideal video of this section in synchronization. Alternatively, the video generation unit 44 may play back only a portion, such as the arms and the waist, of the virtual ideal video where the difference between skeletal poses of the subject and the master is large in enlarged form. In this case, the video generation unit 44 may select, for example, the largest of the averages $\Delta A_{ave}$ to $\Delta H_{ave}$ of the differences calculated by the score calculation unit 33 regarding the eight joint angles indicated by reference symbols A to H in FIG. 3, and play back the actual video and the virtual ideal video in synchronization, with a portion around the selected joint being enlarged.

The feeling evaluator 50 is composed of a facial recognition unit 51, a pulse-wave analysis unit (a pulse-wave analyzer) 52, and a feeling determination unit (a feeling determiner) 53, as shown in FIG. 2. The feeling evaluator 50 executes facial recognition on the actual video captured by the camera 4, and detects a pulse wave from the skin color of the subject' face. Additionally, the feeling evaluator 50 determines the category of the subject's feeling during the subject's dance movements (during playback of a piece of music and recording by the recorder 20) at certain intervals, e.g., every 30 seconds, based on the degree of variations in pulse intervals, and calculates a score regarding feelings (hereafter, a "mental score").

The facial recognition unit 51 applies an edge detection algorithm or a feature extraction algorithm to the still images constituting the subject's actual video captured by the camera 4, thereby analyzing facial features and identifying an exposed skin portion, such as the forehead, as a measurement region. The facial recognition unit 51 outputs time-series data indicating the skin color of the measurement region to the pulse-wave analysis unit 52.

The pulse-wave analysis unit 52 first extracts a pulse wave signal of the subject from the time-series data obtained from the facial recognition unit 51. Since capillary arteries densely exist, for example, inside the human forehead, luminance of a face image varies in synchronization with the subject's blood flow. In particular, variations in intensity of green light of the image reflect the pulse wave (variations in blood flow) most. Thus the pulse-wave analysis unit 52 uses a band-pass filter transmitting frequencies of human pulse waves approximately from 0.5 to 3 Hz to extract a pulse wave signal from the component of variations in intensity of green light of the time-series data.

Figure 9A:
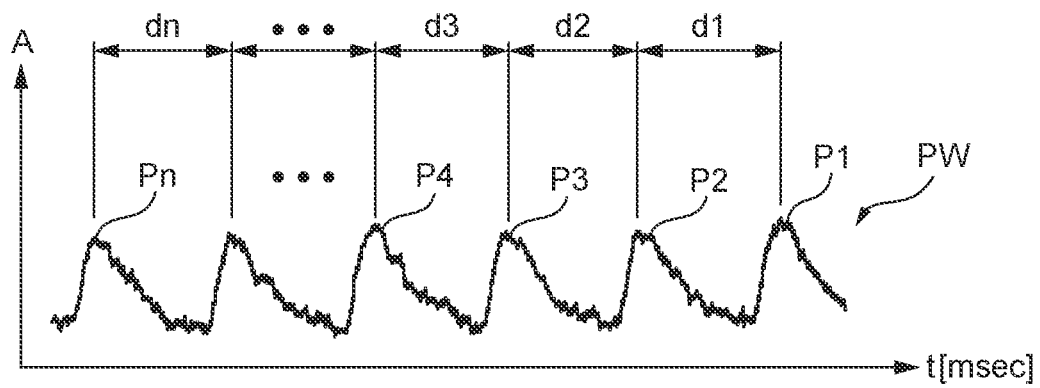
FIGS. 9A, 9B, and 9C are graphs showing an example of the waveform of a pulse wave signal PW, variations in pulse intervals, and changes in positive and negative feelings of a subject.

FIG. 9A is a graph showing an example of the waveform of a pulse wave signal PW. The abscissa t and the ordinate A represent time (milliseconds) and the intensity of amplitude of the pulse wave, respectively. As shown in FIG. 9A, the pulse wave signal PW is a triangular wave reflecting variations in blood flow resulting from a heartbeat. Intervals between peaks P1 to Pn of the blood flow are denoted by pulse intervals d1 to dn. The pulse-wave analysis unit 52 detects the peaks P1 to Pn of the extracted pulse wave signal PW, calculates the pulse intervals d1 to dn in milliseconds, and further generates time-series data of pulse intervals from the pulse intervals d1 to dn.

Figure 9B:
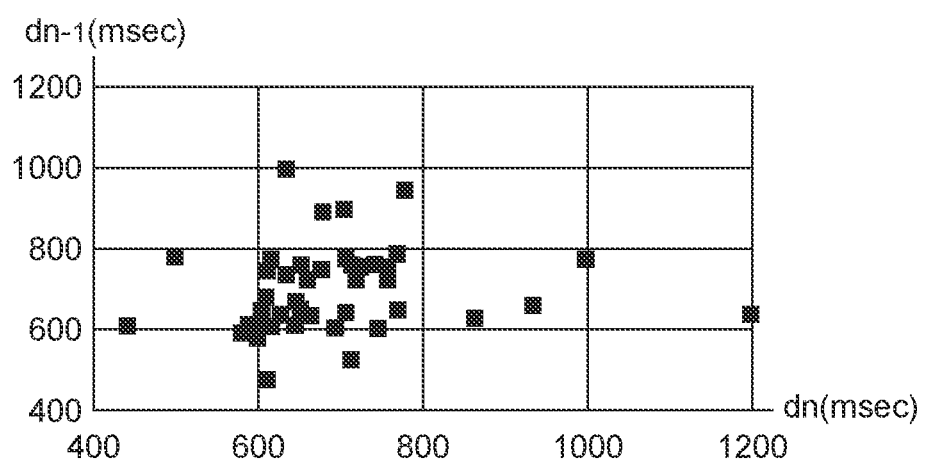

FIG. 9B is a graph showing an example of variations in pulse intervals. This graph is called a Lorentz plot and made by plotting the time-series data of pulse intervals at coordinates (dn, dn−1) for n=1, 2, . . . ; the abscissa and the ordinate represent pulse intervals dn and dn−1 (both in milliseconds), respectively. It is known that the degree of variations of dots in the graph of FIG. 9B reflects positive and negative feelings of the subject.

The pulse-wave analysis unit 52 further calculates a maximum Lyapunov exponent Λ, which is an index indicating the degree of variations in the subject's heartbeat intervals, using the generated time-series data, i.e., coordinates (dn, dn−1) in the Lorentz plot of FIG. 9B, at certain intervals, e.g., every 30 seconds or every 32 beats of the pulse wave, by Expression 1 below.

$$\lambda = \frac{1}{M}\sum_{k=1}^{M} \log_2 \frac{d(k)}{d(k-1)}$$ Expression 1

M denotes the total sampling time in the pulse intervals d1 to dn, and d denotes the distance between patterns of the time-series data at times k and k−1 (distance on the two-dimensional plane of the Lorentz plot).

The feeling determination unit 53 determines whether the subject has a negative feeling with brain fatigue, anxiety, or depression, or a positive feeling free from brain fatigue, anxiety, and depression, based on the maximum Lyapunov exponent λ calculated by the pulse-wave analysis unit 52, at the same intervals as the pulse-wave analysis unit 52. The value of the maximum Lyapunov exponent λ in Expression 1 is negative and large in magnitude in the case of the negative feeling, and is not less than zero or negative and small in magnitude in the case of the positive feeling. Thus, if the calculated maximum Lyapunov exponent λ satisfies Expression 2 below, the feeling determination unit 53 determines that the subject has a negative feeling; if λ does not satisfy Expression 2, it determines that the subject has a positive feeling.

$$\lambda \leq \lambda t$$ Expression 2

λt (<0) is an appropriate threshold set for feeling determination. The feeling determination unit 53 stores the result of determination in the storage 70.

Instead of the two categories of the positive and negative feelings, the feeling determination unit 53 may determine, for example, which of four categories, "positive feeling (free from stress)", "active", "slightly negative feeling (slight fatigue)", and "negative feeling (fatigue)", the subject's feeling belongs to, depending on the magnitude of the maximum Lyapunov exponent Λ. The feeling determination unit 53 may display the determined categories of the subject's feeling sequentially on the monitor 2C during the subject's dance movements.

Figure 9C:
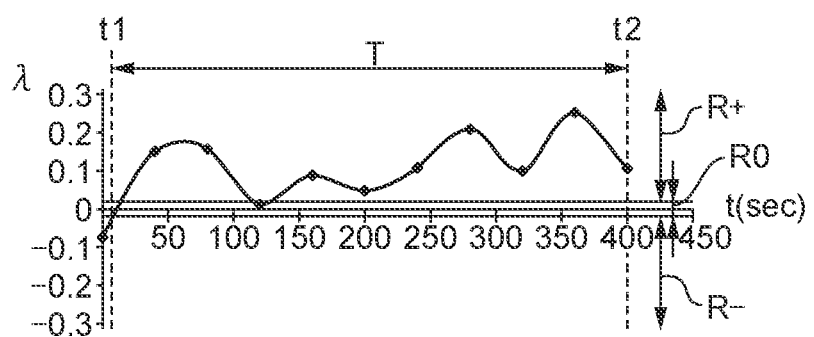

FIG. 9C is a graph showing an example of changes in positive and negative feelings of a subject. The abscissa t and the ordinate λ represent time (seconds) and the maximum Lyapunov exponent, respectively. The regions R+ (λ>0) and R− (λ<0) in the graph correspond to the positive and negative feelings, respectively, and the region RO (λ≈0) therebetween corresponds to a feeling intermediate between the positive and negative feelings. Assume that the subject performed dance movements during the period T between times t1 and t2. In the illustrated example, of the results of ten times of feeling determination, one was the intermediate feeling and nine were the positive feeling.

The feeling determination unit 53 calculates a mental score of the subject, depending on frequency of occurrence of the positive feeling during recording by the recorder 20, and displays its value on the monitor 2C of the karaoke device 2. For example, the feeling determination unit 53 refers to the storage 70 to calculate the rate of occurrence of the positive feeling, which is defined as "(the number of times of determination that the feeling is positive)/(the number of times of determination by the feeling determination unit 53)", as the mental score. In the example of FIG. 9C, the rate of occurrence of the positive feeling is 90%, and thus the mental score is 90.

Regardless of the dance score, a low mental score suggests that the subject is not enjoying dancing. Thus, presentation of both the dance and mental scores provides the subject with indices to find a suitable piece of music to which he/she can dance well without feeling pain. One possible way to determine the category of the feeling is, for example, to attach a sensor to a microphone for karaoke and to detect a pulse wave while a singer is holding the microphone. However, since the microphone cannot be held during dancing, such a technique is inappropriate. In contrast, the feeling evaluator 50 can calculate a mental score in a non-contact manner, and is thus applicable to dancing. Additionally, since the subject's face is shown in a video of dance movements and a pulse wave can be detected from this video, a single camera is enough. Thus, the technique of the feeling evaluator 50 also has the advantage of eliminating the need for a separate sensor for detecting a pulse wave.

The display controller 60 outputs an actual video of the subject captured by the recorder 20, a dance score calculated by the score calculation unit 33, a virtual ideal video generated by the video generation unit 44, and a mental score calculated by the feeling determination unit 53 to the karaoke device 2 and displays them on the monitor 2C in response to instructions from the recorder 20, the analyzer 30, the generator 40, and the feeling evaluator 50.

The storage 70 is mainly composed of an ideal-data storage unit 71 and a training-data storage unit 72. The ideal-data storage unit 71 contains the ideal skeletal pose information for each piece of music. In the case that the karaoke device 2 is karaoke-on-demand, the ideal-data storage unit 71 may be provided together with the music database 11 on a cloud, separately from the evaluation device 3 and the karaoke device 2. The training-data storage unit 72 contains a group of image data generated by the skeletal-pose analysis unit 31 (in which images of an actual video and skeletal poses are juxtaposed) and information on the trained model generated by the model generation unit 42. The storage 70 further contains information necessary for operation of the evaluation device 3, such as the subject's actual video captured by the recorder 20 and the category of the subject's feeling determined by the feeling determination unit 53.

FIGS. 10A to 10C illustrate examples of display of the dance and mental scores. These scores may be displayed as numerical values, as shown in FIG. 10A, or displayed using figures such as bars extended with the numerical values, as shown in FIG. 10B. FIG. 10B shows an example in which a singing score and the total of the dance, mental, and singing scores are calculated and displayed in addition to the dance and mental scores. FIGS. 10A and 10B show examples of display that appears after dance movements; but as shown in FIG. 10C, temporary data of the dance and mental scores may be displayed in real time during the subject's dance movements in the manner of representation of musical intervals. Alternatively, the dance and mental scores may be displayed on the subject's actual video or the virtual ideal video. Calculation and display of the dance and mental scores are not essential, and one or both of the score calculation unit 33 and the feeling evaluator 50 may be omitted.

Figure 11:
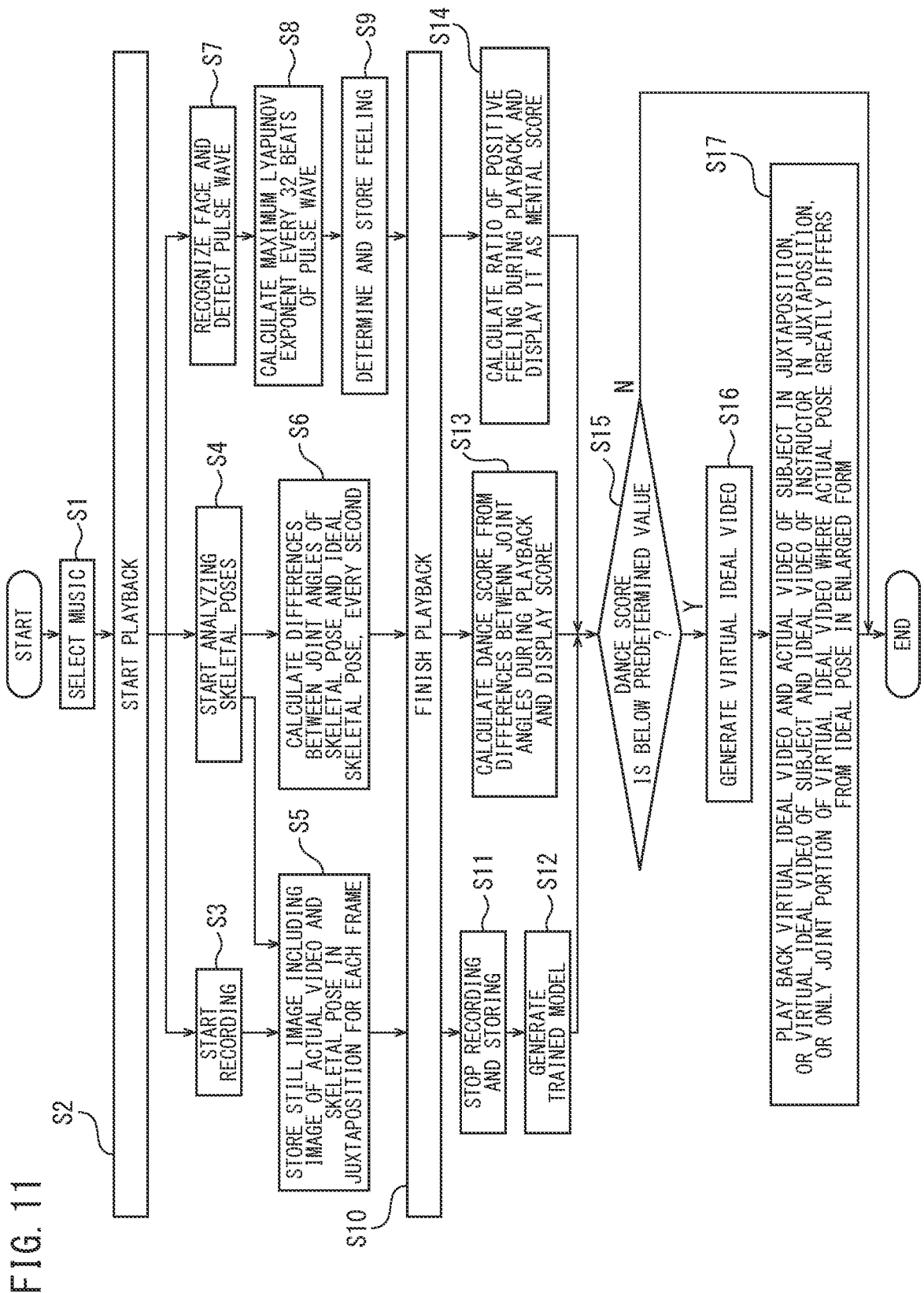
FIG. 11 is a flowchart showing an operational example of the karaoke system 1.

FIG. 11 is a flowchart showing an operational example of the karaoke system 1. First, the music selector 12 of the karaoke device 2 selects a piece of dance karaoke music in response to a user operating the remote control 2D (S1), and the player 14 starts playback of this piece of music (S2). At this time, the player 14 may also display, for example, an actual video of the master's ideal dance movements on the monitor 2C. With the start of playback, the subject starts dance movements, and the camera 4 and the recorder 20 start video capturing and recording, respectively (S3).

The skeletal-pose analysis unit 31 starts analyzing skeletal poses in the actual video captured by the camera 4 (S4), and stores a still image including an image of the actual video and a skeletal pose in juxtaposition in the training-data storage unit 72 for each frame (S5). The difference determination unit 32 calculates the differences between joint angles of skeletal poses of the ideal skeletal pose information regarding a target piece of music and the skeletal pose information extracted by the skeletal-pose analysis unit 31, every second (S6). The facial recognition unit 51 executes facial recognition on the actual video captured by the camera 4, and the pulse-wave analysis unit 52 starts detecting a pulse wave (S7). The pulse-wave analysis unit 52 calculates the maximum Lyapunov exponent $\lambda$ every 32 beats of the pulse wave (S8), and the feeling determination unit 53 determines which of four categories the subject's feeling belongs to, depending on its value, and stores the result in the storage 70 (S9).

Thereafter, when playback of the selected piece of karaoke music is finished (S10), the camera 4, the recorder 20, and the skeletal-pose analysis unit 31 stop video capturing, recording, and storing of still images, respectively (S11). The image extraction unit 41 extracts a predetermined number of images such that the coordinates or the joint angles of the arms or the legs differ by more than a reference value from the group of still images (group of image data) stored in the training-data storage unit 72, and the model generation unit 42 executes deep learning to generate a trained model (S12). The score calculation unit 33 calculates a dance score from the average of the differences between joint angles during playback of the piece of music, and displays it on the monitor 2C (S13). The feeling determination unit 53 calculates the rate of occurrence of the positive feeling during playback of the piece of music, and displays it as a mental score on the monitor 2C (S14).

If the dance score calculated in S13 is not lower than a reference value (No in S15), the karaoke system 1 terminates operation. If the dance score is lower than the reference value (Yes in S15), the video generation unit 44 generates a virtual ideal video (S16). Additionally, the video generation unit 44 plays back, for example, the virtual ideal video and the actual video of the subject in juxtaposition, or the virtual ideal video of the subject and an actual video of ideal dance movements of a master (instructor) in juxtaposition, or only a joint portion of the virtual ideal video where the difference between skeletal poses of the subject and the master is large in enlarged form (S17). The karaoke system 1 then terminates operation.

Contrary to the determination in S15, the virtual ideal video may be displayed as a reward if the dance score is not higher than the reference value, i.e., if the difference between skeletal poses of the subject who has practiced dancing and the master has become small. The model generation unit 42 may generate a trained model, based on a video of the subject performing reference movements, such as radio calisthenics, instead of a video of the subject actually dancing to a piece of karaoke music.

The evaluation device 3 shows an ideal dance video in the form of the subject's video rather than the master's video, thereby enhancing the subject's motivation to keep dancing. The device enables the subject to compare his/her videos to realize the difference between actual and ideal dance movements, which clarifies points to be corrected and thus improves efficiency of learning dancing. Once a trained model is generated, virtual ideal videos for multiple pieces of music can be easily generated by inputting ideal skeletal pose information. Additionally, the evaluation device 3 can be externally attached to an existing karaoke device 2 and used without greatly converting the karaoke device, which provides the advantages of lowering the cost of fabrication and being flexible.

The above description relates to the case in which the subject is a single person. However, when two or more persons are dancing side by side (when the subject is a group) also, a virtual ideal video can be generated by a process similar to that described above. When there are multiple subjects, the skeletal-pose analysis unit 31 extracts skeletal poses of the respective subjects from an actual video of their dance movements captured by the camera 4. This actual video needs to be captured so that the persons do not overlap, to recognize the skeletal poses. The ideal-data storage unit 71 prestores ideal group skeletal pose information representing a series of skeletal poses corresponding to ideal dance movements performed to the same piece of music by as many masters as the subjects.

Figure 12:
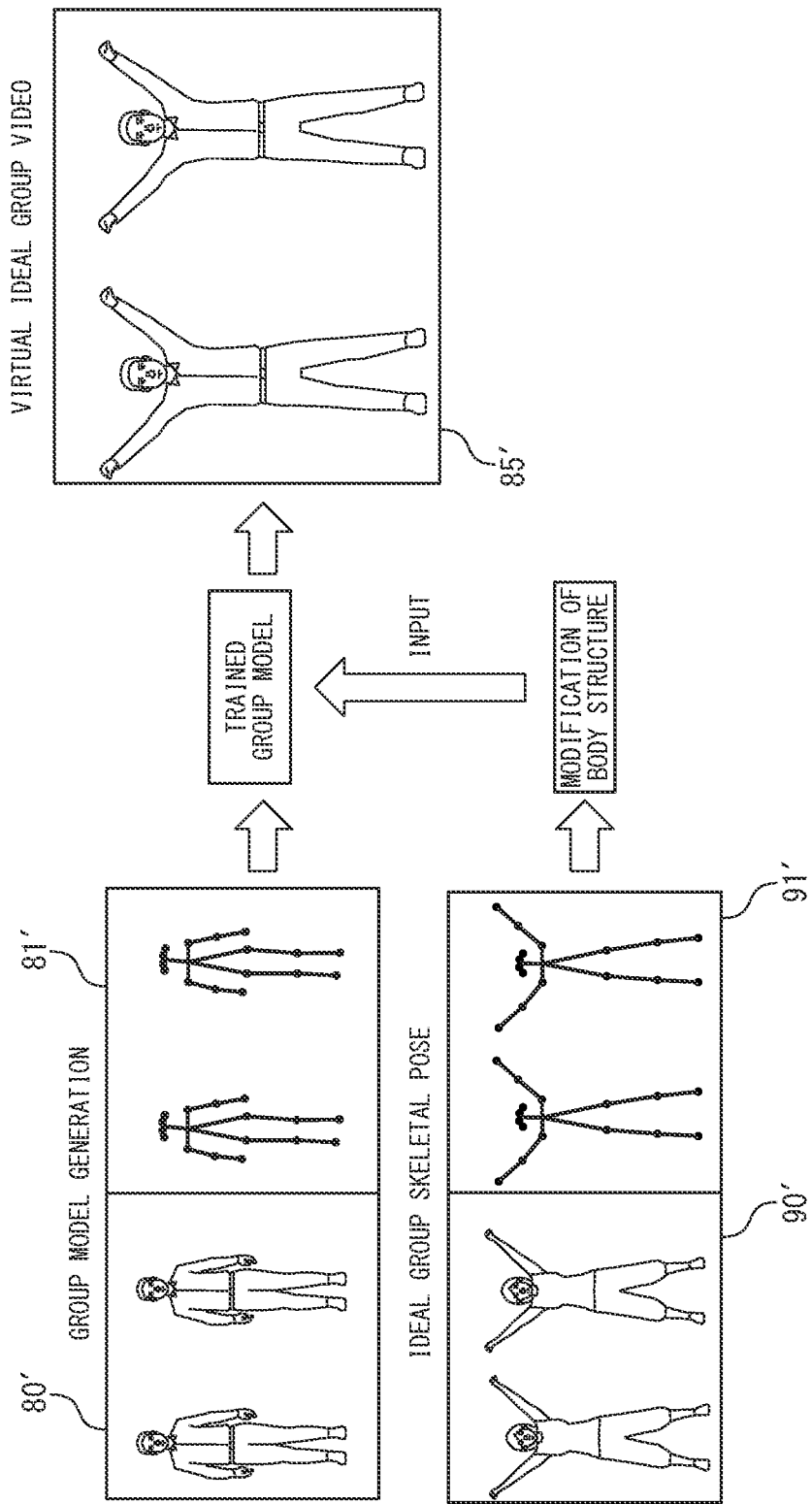
FIG. 12 is a diagram for explaining the functions of the generator 40 for the case that there are multiple subjects.

FIG. 12 is a diagram for explaining the functions of the generator 40 for the case that there are multiple subjects. When there are multiple subjects, the model generation unit 42 learns the relationship between an actual video 80' of the subjects and skeletal poses 81' of the respective persons, based on some still images selected by the image extraction unit 41 from the group of still images constituting the actual video of the subjects, thereby generating a trained group model. For each subject in the video, the image extraction unit 41 selects still images such that the coordinates or the joint angles of the arms or the legs differ. The structure modification unit 43 modifies the lengths of the trunk and the legs of the skeletal poses of each master in the ideal group skeletal pose information to match them to the person in the group corresponding to the master (reference symbols 90' and 91' indicate an actual video and skeletal poses of the masters, respectively). The video generation unit 44 generates a virtual ideal group video 85', which is a video of the subjects performing the same dance movements as the masters, based on the trained group model and the modified ideal group skeletal pose information.

The model generation unit 42 may combine trained models generated separately for the respective subjects to generate the trained group model. The video generation unit 44 may combine virtual ideal videos 85 generated separately for the respective subjects to generate the virtual ideal group video 85'. However, to combine trained models, the arrangement of the subjects in the images needs to be substantially the same as that of the masters in the ideal group skeletal pose information. Alternatively, the storage 70 may contain ideal group skeletal pose information and a trained group model, instead of ideal skeletal pose information and trained models; the video generation unit 44 may generate a virtual ideal video for each individual in the group, using part of this data.

Second Embodiment

Figure 13:
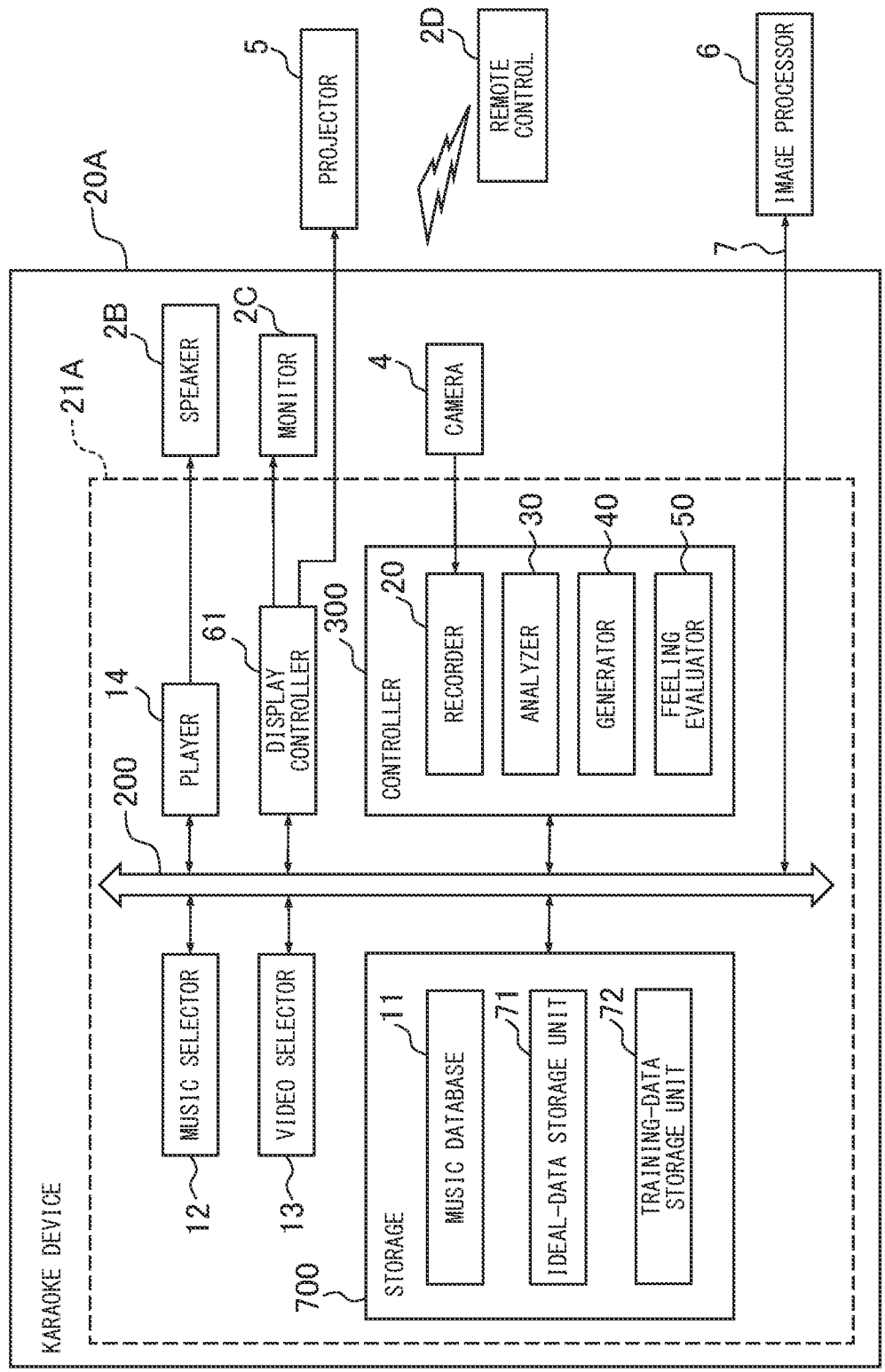
FIG. 13 illustrates the general configuration of a video generation device according to the second embodiment of the present disclosure.

The following describes a video generation device according to the second embodiment of the present disclosure. FIG. 13 illustrates the general configuration of a video generation device according to the second embodiment of the present disclosure. In the example of the video generation device described in the first embodiment, the evaluation device configured with hardware is provided separately from the karaoke device. In the video generation device according to the second embodiment, all of the functions of the evaluation device are implemented in a body 21A of a karaoke device 20A as software. Thus the components in the body 21A according to the second embodiment have the same functions as those in the evaluation device of the video generation device according to the first embodiment.

The video generation device according to the second embodiment is the karaoke device 20A, which is composed of a body 21A, a speaker 2B, a monitor 2C, a remote control 2D, and a camera 4. As its functional blocks, the body 21A includes a music selector 12, a video selector 13, a player 14, a display controller 61, storage 700, and a controller 300, which are connected via a bus 200.

The storage 700 is constructed from, for example, a semiconductor memory or a hard disk whereas the other functional blocks are implemented by a computer program, such as dedicated plug-in software, executed on a microcomputer including a CPU, a ROM, and a RAM.

The storage 700 includes a music database 11, an ideal-data storage unit 71, and a training-data storage unit 72. The music database 11 contains pieces of karaoke music and videos. The ideal-data storage unit 71 contains ideal skeletal pose information representing, for each piece of music, a series of skeletal poses corresponding to ideal dance movements to the piece of music. The training-data storage unit 72 contains a group of image data generated by a skeletal-pose analysis unit included in an analyzer 30 and information on a trained model generated by a model generation unit included in a generator 40.

The music selector 12 and the video selector 13 select music and a video stored in the music database 11 in response to a user operating the remote control 2D. The player 14 outputs the music selected by the music selector 12 to the speaker 2B and the video selected by the video selector 13 to the monitor 2C, and plays them back. The camera 4 is provided for the karaoke device 2, and captures a video of a subject performing dance movements to a piece of music.

The controller 300 includes a recorder 20, an analyzer 30, a generator 40, and a feeling evaluator 50. The recorder 20 stores data of an actual video captured by the camera 4 in the storage 700 to record a video. The camera 4 and the recorder 20 record an actual video of dance movements performed by a subject to a piece of music played back by the karaoke device 20A.

The analyzer 30 analyzes skeletal poses of the subject in an actual video captured by the camera 4, determines the differences between individual joint angles of these skeletal poses and corresponding ideal values, and calculates a dance score. The analyzer 30 includes a skeletal-pose analysis unit that extracts skeletal pose information representing a series of skeletal poses corresponding to the subject's dance movements from a group of still images constituting the actual video.

When the dance score is not higher than a reference value, the generator 40 learns the relationship between the actual video and the skeletal pose of the subject to generate a trained model. The generator 40 then modifies the prestored ideal skeletal pose information to match it to the subject's body structure, and generates a virtual ideal video, which is a video of the subject performing the same dance movements as the master, based on the trained model and the modified ideal skeletal pose information.

The feeling evaluator 50 executes facial recognition on the actual video captured by the camera 4, and detects a pulse wave from the skin color of the subject' face. Additionally, the feeling evaluator 50 determines the category of the subject's feeling during the subject's dance movements at certain intervals, e.g., every 30 seconds, based on the degree of variations in pulse intervals, and calculates a mental score.

The display controller 61 displays an actual video of the subject captured by the recorder 20, a dance score, a virtual ideal video, and a mental score on the monitor 2C in response to instructions from the recorder 20, the analyzer 30, the generator 40, and the feeling evaluator 50.

The monitor 2C provided for the karaoke device 20A as standard may be a liquid crystal display. When a video is displayed on a screen larger than the monitor 2C, the karaoke device 20A may be provided with a projector 5 and output the video to the projector 5 rather than to the monitor 2C.

When skeletal pose information is extracted from a captured dance video of the subject, it is preferable to use as many images of the captured video as possible. However, to process many images at high speed, the video generation unit of the generator 40 (see FIG. 2) may be overloaded. Thus the video generation device preferably further includes an image processor that generates a virtual ideal video for the video generation unit. The image processor 6 can be connected to the body 21A via a cable 7. As the image processor 6, a graphics processing unit (GPU) can be used. The use of the image processor enables high-speed image processing, which enables processing many images at high speed and displaying the generated virtual ideal video smoothly. As the GPU, for example, RTX2070 manufactured by NVIDIA Corporation can be used. As the cable 7, a high-speed general-purpose data transfer cable, such as Thunderbolt3, is preferably used.

Since all of the functions of the evaluation device are implemented in the body of the karaoke device as software, the video generation device according to the second embodiment can be downsized. Additionally, since the image processor is externally attached, an image processor with an appropriate throughput can be selected and used depending on the amount of image data to be processed.

Third Embodiment

Figure 14:
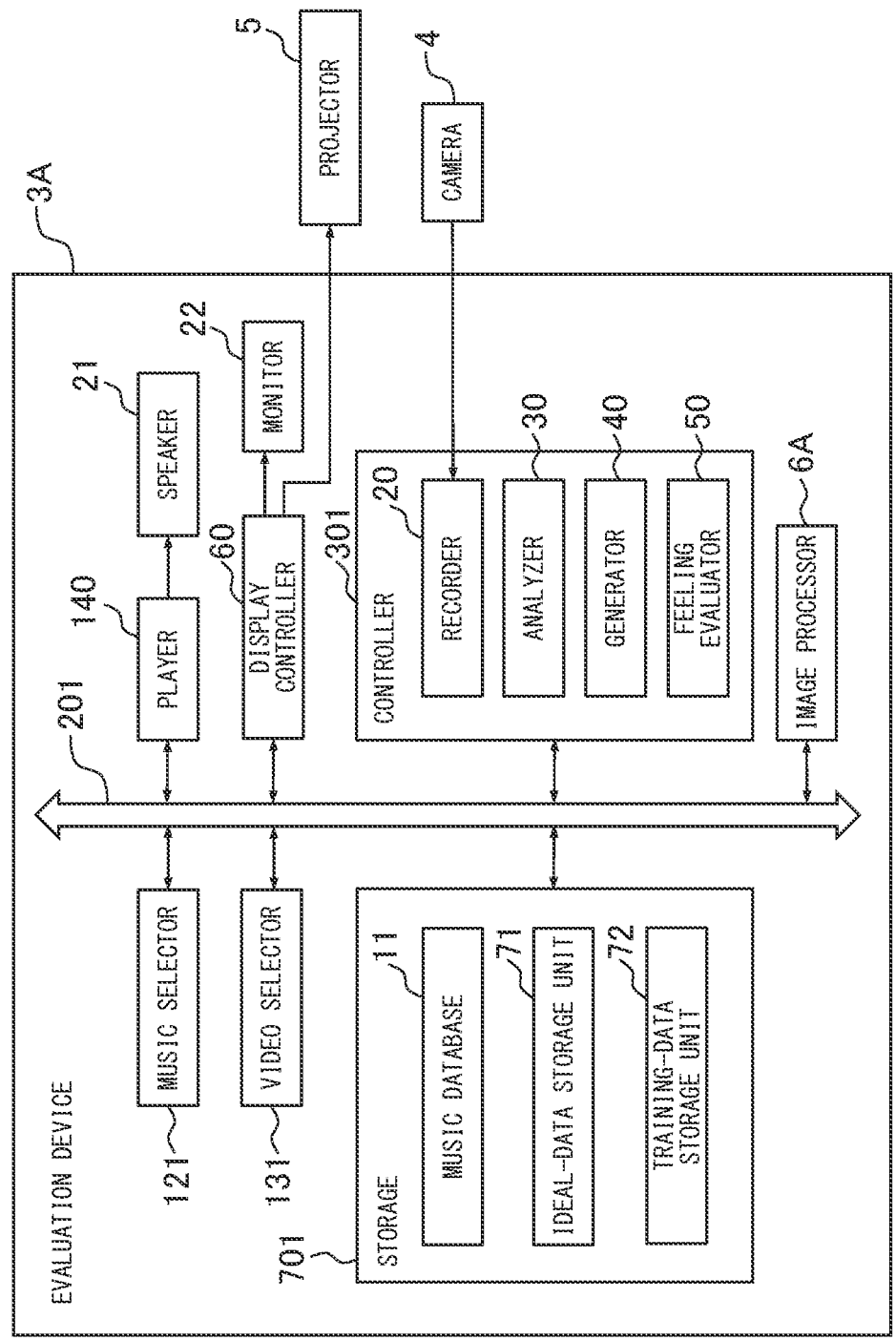
FIG. 14 illustrates the general configuration of a video generation device according to the third embodiment of the present disclosure.

The following describes a video generation device according to the third embodiment. FIG. 14 illustrates the general configuration of a video generation device according to the third embodiment. In the example of the video generation device described in the first embodiment, the evaluation device is used in combination with the karaoke device. In the third embodiment, a stand-alone evaluation device is used as a video generation device independently of a karaoke device.

The video generation device according to the third embodiment includes an evaluation device 3A, a camera 4, and a projector 5. The evaluation device 3A achieves functions similar to those of the evaluation device 3, which is the video generation device according to the first embodiment. The evaluation device 3A may be, for example, a personal computer (PC).

The evaluation device 3A includes a music selector 121, a video selector 131, a player 140, a display controller 60, storage 701, a controller 301, and an image processor 6A, which are connected via a bus 201. The evaluation device 3A further includes a speaker 21 and a monitor 22. The evaluation device 3A can record a subject's actual video captured by the camera 4, generate a virtual ideal video, and display it on the monitor 22.

The storage 701 is constructed from, for example, a semiconductor memory or a hard disk whereas the other functional blocks are implemented by a computer program executed on a microcomputer including a CPU, a ROM, and a RAM.

The storage 701 includes a music database 11, an ideal-data storage unit 71, and a training-data storage unit 72. The music database 11 contains music and videos. The music selector 121 and the video selector 131 select music and a video stored in the music database 11 in response to a user operating a keyboard or a mouse. The player 140 outputs the music selected by the music selector 121 to the speaker 21 and the video selected by the video selector 131 to the monitor 22, and plays them back. The camera 4 is externally attached to the evaluation device 3A, and captures a video of a subject performing dance movements to a piece of music.

The controller 301 includes a recorder 20, an analyzer 30, a generator 40, and a feeling evaluator 50. The recorder 20 stores data of an actual video captured by the camera 4 in the storage 701 to record a video. The camera 4 and the recorder 20 record an actual video of dance movements performed by a subject to a piece of music played back by the evaluation device 3A.

The operation of the analyzer 30, the generator 40, the feeling evaluator 50, and the display controller 60 is the same as that of the corresponding components in the video generation device according to the first embodiment; thus, detailed description thereof is omitted.

The monitor 22 provided for the evaluation device 3A as standard may be a liquid crystal display. When a video is displayed on a screen larger than the monitor 22, the evaluation device 3A may be provided with a projector 5 and output the video to the projector 5 rather than to the monitor 22.

As the image processor 6A, a GPU can be used. The image processor 6A enables high-speed image processing, which enables displaying the generated virtual ideal video smoothly.

The video generation device according to the third embodiment, which do not use a karaoke device, has a simple configuration and can be used at, for example, a dance studio in a private room.

Fourth Embodiment

Figure 15:
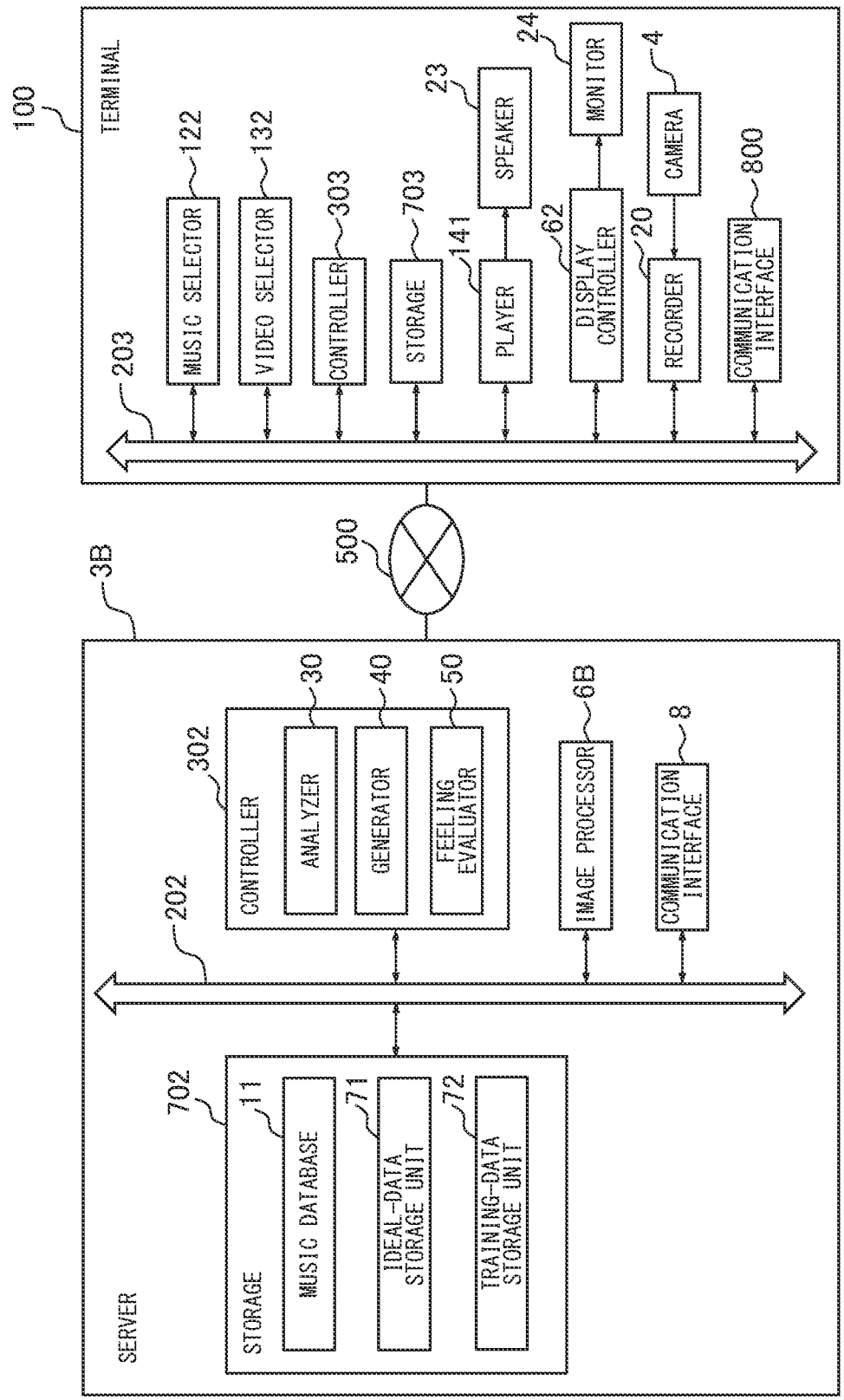
FIG. 15 illustrates the general configuration of a video generation device according to the fourth embodiment of the present disclosure.

The following describes a video generation device according to the fourth embodiment. FIG. 15 illustrates the general configuration of a video generation device according to the fourth embodiment. In the example of the video generation device described in the third embodiment, the video generation device is placed, for example, in a studio and used by a subject. In this case, the subject needs to go to the studio where the video generation device is placed. However, some subjects wish to use the video generation device anywhere. For example, some people wish to show a video of ideal movements for rehabilitation to elderly people who are rehabilitated at their home, thereby enhancing their motivation for the rehabilitation. Thus the video generation device according to the fourth embodiment further includes a communication interface that receives an actual video of a subject from an external terminal and that transmits a virtual ideal video of the subject to an external terminal.

The video generation device according to the fourth embodiment includes an evaluation device 3B and a terminal 100, which are connected through the Internet 500. As the terminal 100, a terminal, such as a smartphone, a tablet device, a feature phone, a personal digital assistant (PDA), a desktop PC, or a notebook PC, can be used.

The evaluation device 3B is configured as a server and includes storage 702, a controller 302, an image processor 6B, and a communication interface 8, which are connected via a bus 202. The evaluation device 3B achieves functions similar to those of the evaluation device 3 described above.

The storage 702 is constructed from, for example, a semiconductor memory or a hard disk whereas the controller 302 is implemented by a computer program executed on a microcomputer including a CPU, a ROM, and a RAM.

The storage 702 includes a music database 11, an ideal-data storage unit 71, and a training-data storage unit 72. The music database 11 contains music and videos.

The controller 302 includes an analyzer 30, a generator 40, and a feeling evaluator 50. The operation of the analyzer 30, the generator 40, and the feeling evaluator 50 is the same as that of the corresponding components in the video generation device according to the first embodiment; thus, detailed description thereof is omitted.

As the image processor 6B, a GPU can be used. The image processor 6B enables high-speed image processing, which enables displaying the generated virtual ideal video smoothly.

The communication interface 8 transmits and receives video data to and from the terminal 100 through the Internet 500 by wired or wireless communication.

The terminal 100 includes a music selector 122, a video selector 132, a controller 303, storage 703, a player 141, a display controller 62, a recorder 20, and a communication interface 800, which are connected via a bus 203. The terminal 100 further includes a speaker 23, a monitor 24, and a camera 4. The recorder 20 stores data of an actual video captured by the camera 4 in the storage 703 to record a video.

The music selector 122 and the video selector 132 of the terminal 100 select a piece of music and a video stored in the music database 11 of the evaluation device 3B.

The player 141 outputs the music selected by the music selector 122 to the speaker 23 and the video selected by the video selector 132 to the monitor 24, and plays them back. The camera 4 is incorporated in the terminal 100. The camera 4 and the recorder 20 record an actual video of dance movements performed by a subject to a piece of music played back by the terminal 100.

The actual video representing the subject's dance movements and stored in the storage 703 is transmitted by the communication interface 800 to the server 3B through the Internet 500.

Data of the actual video transmitted to the server 3B is received by the communication interface 8. The controller 302 generates a virtual ideal video from the received actual video, and transmits the generated virtual ideal video to the terminal 100 through the Internet 500. The steps to generate the virtual ideal video from the subject's actual video are similar to those executed by the video generation device according to the first embodiment.

The display controller 62 of the terminal 100 displays the virtual ideal video received from the server 3B on the monitor 24.

The following describes the steps of operation of the video generation device according to the fourth embodiment. FIG. 16 shows a flowchart for explaining the steps of operation of the video generation device according to the fourth embodiment of the present disclosure. The following describes an example in which an elderly person is rehabilitated at home.

First, in step S21, moving images of the subject are captured with the camera 4 of the terminal 100. For example, moving images of the elderly person performing movements, such as squat exercises, to music are captured.

Next, in step S22, the captured moving images are stored in the storage 703 of the terminal 100.

Next, in step S23, the stored moving images are uploaded from the terminal 100 to the server 3B through the Internet 500.

Next, in step S24, a virtual ideal video is generated in the server 3B, based on the uploaded moving images. For example, skeletal poses information on the subject is collected from the moving images uploaded by the subject, and a virtual ideal video of the subject performing correct squat exercises is generated using prepared moving images of ideal squat exercises.

Next, in step S25, the generated virtual ideal video is downloaded from the server 3B to the terminal 100 through the Internet 500.

Next, in step S26, the downloaded virtual ideal video is displayed on the monitor 24 of the terminal 100. The subject watching the virtual ideal video in which he/she is performing correct squat exercises can easily understand how to move his/her body. Additionally, a portion in the virtual ideal video that differs from a corresponding portion in the moving images uploaded by the subject may be highlighted. This enables the subject to easily recognize which part of his/her movements is incorrect. The video generation device according to the fourth embodiment can enhance motivation of elderly people for rehabilitation exercises. The rehabilitation exercises are not limited to squat movements, which are an example; the device can also be applied similarly to other rehabilitation exercises.

In the above-described example, a virtual ideal video is generated from the subject's moving images captured with the terminal 100. However, dance and mental scores may be further calculated as in the video generation device according to the first embodiment.

The video generation device according to the fourth embodiment enables the subject to generate a virtual ideal video anywhere from an actual video.

In the above-described examples, it is from a group of still images constituting an actual video of a human subject that skeletal pose information representing a series of skeletal poses corresponding to the subject's dance movements is extracted. However, the invention is not limited to such examples. More specifically, as long as a skeleton can be extracted, skeletal pose information may be extracted from things other than humans, such as a puppet or an animation character. In other words, the "subject" is not limited to a human, and includes everything from which skeletal pose information can be extracted. For example, when being applied to animation, the device can extract skeletal pose information on an animation character, and generate a virtual ideal video of the animation character performing dance movements matching ideal skeletal pose information, based on the extracted skeletal pose information.

In the above-described examples, the virtual ideal video is a dance video. However, the virtual ideal video is not limited thereto, and may be a video of other movements performed at predetermined timings, such as a pitching form of baseball. For example, when being applied to a pitching form, the device can generate a virtual ideal video of a subject performing the same pitching form as a celebrated player, using ideal skeletal pose information generated from pitching movements of the celebrated player.

In the illustrated examples, dance movements are performed to a piece of music. However, the invention is not limited to such examples, and dance movements may be performed to a predetermined rhythm for synchronization. For example, dance movements may be performed to predetermined rhythmic sounds produced, for example, by a metronome.

In the above-described examples, the actual video is a video of the subject's dance movements, which is captured with a camera, similar to the virtual ideal video. However, the actual video is not limited thereto, and may be a video of movements other than dance movements if skeletal poses information on the subject can be extracted therefrom. Then, for example, from a video of a subject who cannot perform dance movements, a virtual ideal video of the subject performing ideal dance movements can be generated. In this case, to generate a smooth virtual video, it is preferable that the movements in the actual video be close to those in the virtual ideal video.

The invention claimed is:

1. A video generation device comprising:
   storage that contains ideal skeletal pose information representing, for each of predetermined rhythms, a series of skeletal poses corresponding to ideal movements performed at predetermined timings to the predetermined rhythm;
   a recorder that records an actual video of movements performed by a subject at predetermined timings to a predetermined rhythm played back;
   a skeletal-pose analysis unit that extracts skeletal pose information representing a series of skeletal poses corresponding to the movements performed by the subject at predetermined timings from a group of still images constituting the actual video;
   a model generation unit that generates a trained model of images of the subject corresponding to skeletal poses, based on the group of still images and the skeletal pose information; and
   a video generation unit that generates and outputs a virtual ideal video, based on the trained model and the ideal skeletal pose information, wherein the virtual ideal video is a video of the subject performing movements matching the ideal skeletal pose information at predetermined timings.

2. The video generation device according to claim 1, further comprising a difference determination unit that determines difference between joint angles of skeletal poses of the skeletal pose information and the ideal skeletal pose information, wherein
   the video generation unit outputs the virtual ideal video when the difference is not less than a reference value.

3. The video generation device according to claim 2, wherein the video generation unit selects a section of the predetermined rhythm corresponding to the movements performed by the subject at predetermined timings, based on the magnitude of the difference, and plays back the actual video and the virtual ideal video of the section in synchronization.

4. The video generation device according to claim 2, wherein the difference determination unit determines the difference for each of joints, and
   the video generation unit selects one of the joints, based on the magnitude of the difference, and plays back the actual video and the virtual ideal video in synchronization, with a portion around the selected joint being enlarged.

5. The video generation device according to claim 2, further comprising a score calculation unit that calculates a score of the movements performed by the subject at predetermined timings, depending on the magnitude of the difference.

6. The video generation device according to claim 5, further comprising:
   a pulse-wave analysis unit that extracts a pulse wave signal of the subject from time-series data indicating skin color of the subject in the actual video to calculate an index indicating the degree of variations in pulse intervals; and
   a feeling determination unit that determines whether the subject has a negative feeling with brain fatigue, anxiety, or depression, or a positive feeling free from brain fatigue, anxiety, and depression, based on the index, and that calculates a score regarding feelings of the subject, depending on frequency of occurrence of the positive feeling during movements performed at predetermined timings.

7. The video generation device according to claim 1, further comprising a structure modification unit that calculates the ratio between the lengths of the trunk and the legs of the subject in the actual video and that modifies the lengths of the trunk and the legs of the skeletal poses in the ideal skeletal pose information, depending on the ratio, wherein
   the video generation unit generates the virtual ideal video, based on the trained model and the modified ideal skeletal pose information.

8. The video generation device according to claim 1, further comprising an image extraction unit that extracts some still images from the group of still images, based on a predetermined criterion regarding the angles or positions of joints of skeletal poses corresponding to the respective still images, wherein
   the model generation unit generates the trained model, based on the extracted still images and skeletal poses in the skeletal pose information corresponding to the extracted still images.

9. The video generation device according to claim 1, further comprising an image processor that generates a virtual ideal video for the video generation unit.

10. The video generation device according to claim 1, further comprising a communication interface that receives an actual video of the subject from an external terminal and that transmits a virtual ideal video of the subject to an external terminal.

11. The video generation device according to claim 1, wherein the predetermined rhythms are made by pieces of music.

12. The video generation device according to claim 1, wherein the movements performed at predetermined timings are dance movements.

* * * * *